United States Patent [19]

St-Arnaud et al.

[11] Patent Number: 6,096,876

[45] Date of Patent: Aug. 1, 2000

[54] 1-α-HYDROXYLASE MATERIALS AND METHODS

[75] Inventors: René St-Arnaud; Francis H. Glorieux, both of Montréal, Canada

[73] Assignee: Shriners Hospitals for Children, Tampa, Fla.

[21] Appl. No.: 08/906,791

[22] Filed: Aug. 6, 1997

[51] Int. Cl.[7] ........................... C12N 15/12; C12N 15/53; C12N 15/85; C12N 15/90

[52] U.S. Cl. ........................ 536/23.2; 435/69.1; 435/189; 435/252.3; 435/320.1; 435/455; 514/44; 536/23.5; 536/24.5; 800/8; 800/9; 800/18

[58] Field of Search ...................................... 435/440, 325, 435/189, 320.1, 69.1, 252.3, 455; 536/23.2, 23.5; 514/44; 800/8, 9, 18

[56] References Cited

U.S. PATENT DOCUMENTS 4,554,106  11/1985  DeLuca et al. ....................... 260/397.2

FOREIGN PATENT DOCUMENTS 0 890 643 A2   1/1999   European Pat. Off. .
3232493       10/1991   Japan .
WO 90/01321    2/1990   WIPO .

OTHER PUBLICATIONS

Chen et al., "Cloning of the human 1,25–dihydroxyvitamin D–3 24–hydroxylase gene promoter and idenification of two vitamin D–responsive elements," *Biochimica et Biophysica Acta*, 1263:1–9 (1995).

F.H. Glorieux, "Pseudo–vitamin D deficiency rickets," *Journal of Endocrinology*, 154:S75–S78 (1997).

Ohyama et al., "Identification of a Vitamin D–responsive Element in the 5'–Flanking Region of the Rat 25–Hydroxyvitamin $D_3$24–Hydroxylase Gene," *J. Biological Chemistry*, 269(14):10545–10550 (Apr. 8, 1994).

*Primary Examiner*—Ponnathapu Achutamurthy
*Assistant Examiner*—William W. Moore
*Attorney, Agent, or Firm*—Marshall, O'Toole, Gerstein, Murray & Borun

[57] ABSTRACT

The invention is directed to polynucleotides encoding all or a fragment of the P450 moiety of vitamin D1 α-Hydrdoxylase and polypeptides encoded thereby.

It encompasses antibodies to the polynucleotides and hybridizing polynucleotides. The polynucleotides and polypeptides are used in methods of diagnosing and treating vitamin D-related disorders and of producing vitamin D metabolites. The invention also encompasses expression vectors and animal cells comprising the polynucleotides.

18 Claims, 18 Drawing Sheets

HUMAN EXON 58-

```
ttggcgtggg cacaggtcaa gtccccgccc agggtatcca agtgtccgct gtgtccgctc          60
ccccagGTGC AGGGCGCCGC GCACTTCGGG CCGGTGTGGC TAGCCAGCTT TGGGACAGTG   120

CGCACCGTGT TACGTGGCTG CCCCTGCACT CGTCGAAGAA CTGCTGCGAC ANGAAGGAAC   180

CCNGGCCGAA CGCTGCAGCT TCTCGCCCTG GAANGAGCGC GCCGCTGCCG CCAGCGGCTT   240

GCGACTGCTC ATGCTTA                                                                                          257
```

HUMAN EXON 785-957

```
agtattcacg tgcttttttac caacgcagTT CAGAGGCACG TGGAGCGGCG AGAGGCAGAG           60

GCAGCCATGA GGAACGGAGG ACAGCCNGAG AAGGACTTGG AGTCTGGGGC GCACCTGACC   120

CAATTCNTGT TCCGGGAAGA GTTGCCTGCC CAGTCCATCC TGGGAAATGT GACAGAGTTG   180

CTATTGGCGG GAGTGGACAC Ggtgaggttc tccctccgtg ctgtgagccg gttccagggc   240
ttagcctccg cagactccgg ctccattttt ctgttgcagg ggatccatta tggccacgta         300
gaccagcttg gcttagcacc ctgtagcccc agactcttcc ataatctgca ccctctgctg        360
ggttctcaca cccaacacct ctcttgcttt cacatgtttt tcag                                       404
```

HUMAN EXON 958-1130

```
GTGTCCAACA CGCTCTCTTG GGCTCTGTAT GAGCTCTCCC GGCACCCCGA AGTCCAGACA  60

GCACTCCACT CAGAGATCAC AGCTGCCCTG AGCCCTGGCT CCAGTGCCTA CCCCTCAGCC  120

ACTGTTCTGT CCCAGCTGCC CCTGCTGAAG GCGGTGGTCA AGGAAGTGCT AAGgtgaggg   180
ggaaggagag gaggaacaag angaaatgcc aaggaagggc tgggga                              226
```

```
GGCACGAGCA CAAACATGAC CCAGGCAGTC AAGCTCGCCT CCAGAGTCTT CCATCGAGTC  60

CAACTGCCTT CTCAGCTGGG CAGTGACTCG GTTCTCCGGA GTTTATCTGA TATCCCTGGG  120

CCCTCTACAC CTAGCTTCCT GGCTGAACTC TTCTGCAAAG GGGGGCTGTC CAGGCTACAT  180

GAACTGCAGG TGCATGGCGC TGCGCGGTAC GGGCCAATAT GGTCCGGCAG CTTCGGGACA  240

CTTCGCACAG TTTATGTGGC CGACCCTGCA CTTGTAGAGC AGCTCCTGCG ACAAGAAAGT  300

CATTGTCCAG AGCGCTGTAG TTCTCATCTT GGTCAGAGCA CCGTCGCCAG CCACCAGCGG  360

GCTTGCGGGT TGCTAACGGC GGATGGTGAA GAATGGCAAG AGGCTCCGAA GTCTCCTGGC  420

CCCGCATCTC CTCCGACCTC AAGCAGCGCC GGCTATGCTG GAACTCTGGA CAGCGTGGTC  480

AGTGACCTCG TGCGACGACT AAGGCGCCAG CGGGGACGTG GCTCTGGGCT ACCGGACCTA  540

GTTCTGGACG TGGCGGGAGA GTTTTACAAA TTTGGCCTAG AAGGCATAGG CGCGGTGCTG  600

CTGGGATCGC GCCTGCGCTG CCTGGAGGCT GAAGTTCCTC CGACACAGA AACCTTCATT  660

GAGGCCGTGG GCTCGGTGTT TGTGTCTACA CTCTTGACCA TGGCAATGCC CAGTTGGCTG  720

CACCGCCTTA TACCCGGACC CTGGGCCCGC CTCTGCAGAG ACTGGAATCA GATGTTTGCC  780

TTTGCCCAGA AGCACGTGGA GCAGCGCGAA GGCGAAGCTG CCGTGAGGAA CCAGGGAAAG  840

CCTGAGGAGG ATTTGCCAAC GGGGCATCAC TTAACCGACT TCCTTTTTCG GGAAAAGGTG  900

TCTGTCCAGT CCATAGTGGG AAATGTGAGA GAGCTACTAC TGGCTGGAGT GGACACGGTA  960

TCCAATACGC TCTCCTGGGC ACTCTATGAG CTCTCCCGGC ACCCGGAAGT CCAGTCTGCA 1020

CTCCACTCTG AGATCACAGG CGCTGTGAAC CCTGGCTCCT ATGCCCACCT CCAAGCCACT 1080

GCTCTGTCCC AGCTACCCCT GCTAAAGGCT GTGATCAAAG AAGTGTTGAG GTTGTACCCT 1140

GTGGTACCTG GAACTCCCG TGTCCAGAC AGAGACATCT GTGTAGGAAA CTATGTTATT 1200

CCCCAAGATA CACTGGTTTC CCTCTGTCAC TATGCCACTT CAAGGGACCC CGCCCAGTTT 1260
```

FIG. 1A

CGGGAACCCA ACTCTTTTAA TCCAGCTCGA TGGCTTGGAG AGGGTCCAGC CCCCCACCCA 1320

TTTGCATCTC TTCCTTTTGG CTTTGGCAAA CGAAGTTGCA TAGGGAGACG CTTGGCAGAG 1380

CTCGAGCTAC AAATGGCGTT GGCCCAGATC TTGACCCATT TTGAGGTGCT GCCTGAGCCA 1440

GGTGCTCTTC CAGTCAAACC CATGACCCGG ACTGTCCTGG TACCTGAGAG GAGCATCCAT 1500

CTCCAGTTTG TAGACAGATA GTCCTGTGGA AGGCAGCTGT CATCATCTCT CTCCAGACTG 1560

GATTTTTCTT ACTATGCACA AGAGGCACAC TCTCCCTCGA GGCCTGTCTG TCTGAGCAAA 1620

CTTCAGGAAG CAGGCCCGGG CCTATCTGTG CTTGACCTGA CTCAGCAGGT ACCACAGAAC 1680

CAGGATCCTT TCTCCTGCTC AGTACCTCTC CTGATCATTC CTCAAGATCC AAAGCCTTCA 1740

GATTTTAACA CATCCTTAAA GGGCCAACTC GGGGGTTAAC TAACAGCCCC AGGCAGCCTG 1800

GGCAGGGATC CCCCACTGAT CCTTCCATGC TTACAGTGTT CACTGACAGC TGTCTAAGCA 1860

TCCATTGCAG CACAAACTAA GTGACTGTGC ACCTGGTCTG CACCTGGTCT GCACCTGGTT 1920

GCGTCTCTGC CTGACCATGT GAGCTCTTTG AGAAGAGTGA TGACTACTGG GCTTTTAGCT 1980

CTTTTCCTTT TTGGGACACA GTCTTGCTAT TGTACTCCAT GCTGTCCTTG AACCCACAAG 2040

CCCTCACCTC ACCTTCCCAA GTGTTGGGTT ACGGACATTA GCTATGCCTG CCAGCTTTAT 2100

TAGTCTTTCT ATCTCCTGCC ATGGTCTATC CCGGCTATT TGATACTATA TATTCTCAGA 2160

TTGAATCTGG ACCATGTGGT AGAAGGGATG ACCACTGACC AGGCTCTACC CACCACTTTA 2220

TCTTAATCTT TTCTCTAGGA AAGTGAATCT CTCCTTGCCT TACAGCATTT TAAAGCTCCC 2280

CTTGGCTGTT CTGCTCTTTA GCCACTCTAA AGTGGATCCA CTCTACTTCT CACCACCCAT 2340

CTTTCTGCAC CCCAGCCTGT CTTTTTATAT TAAAAAAATT GTATTTATTA TGTTTTCAAA 2400

TAAAATGTTT ACTCCTTGAA AAAAAAAAAA AAAAAAAAAA AAAA 2444

FIG. 1B

Met Thr Gln Ala Val Lys Leu Ala Ser Arg Val Phe His Arg Val
1           5              10             15

Gln Leu Pro Ser Gln Leu Gly Ser Asp Ser Val Leu Arg Ser Leu
           20              25             30

Ser Asp Ile Pro Gly Pro Ser Thr Pro Ser Phe Leu Ala Glu Leu
      35              40             45

Phe Cys Lys Gly Gly Leu Ser Arg Leu His Glu Leu Gln Val His
            50              55             60

Gly Ala Ala Arg Tyr Gly Pro Ile Trp Ser Gly Ser Phe Gly Thr
         65              70             75

Leu Arg Thr Val Tyr Val Ala Asp Pro Ala Leu Val Glu Gln Leu
        80              85             90

Leu Arg Gln Glu Ser His Cys Pro Glu Arg Cys Ser Ser His Leu
           95              100            105

Gly Gln Ser Thr Val Ala Ser His Gln Arg Ala Cys Gly Leu Leu
          110             115            120

Thr Ala Asp Gly Glu Glu Trp Gln Glu Ala Pro Lys Ser Pro Gly
         125             130            135

Pro Ala Ser Pro Pro Thr Ser Ser Ser Ala Gly Tyr Ala Gly Thr
           140             145            150

Leu Asp Ser Val Val Ser Asp Leu Val Arg Arg Leu Arg Arg Gln
              155             160            165

FIG. 2A

Arg Gly Arg Gly Ser Gly Leu Pro Asp Leu Val Leu Asp Val Ala
          170               175               180

Gly Glu Phe Tyr Lys Phe Gly Leu Glu Gly Ile Gly Ala Val Leu
          185               190               195

Leu Gly Ser Arg Leu Arg Cys Leu Glu Ala Glu Val Pro Pro Asp
          200               205               210

Thr Glu Thr Phe Ile Glu Ala Val Gly Ser Val Phe Val Ser Thr
          215               220               225

Leu Leu Thr Met Ala Met Pro Ser Trp Leu His Arg Leu Ile Pro
          230               235               240

Gly Pro Trp Ala Arg Leu Cys Arg Asp Trp Asn Gln Met Phe Ala
          245               250               255

Phe Ala Gln Lys His Val Glu Gln Arg Glu Gly Glu Ala Ala Val
          260               265               270

Arg Asn Gln Gly Lys Pro Glu Glu Asp Leu Pro Thr Gly His His
          275               280               285

Leu Thr Asp Phe Leu Phe Arg Glu Lys Val Ser Val Gln Ser Ile
          290               295               300

Val Gly Asn Val Arg Glu Leu Leu Leu Ala Gly Val Asp Thr Val
          305               310               315

Ser Asn Thr Leu Ser Trp Ala Leu Tyr Glu Leu Ser Arg His Pro
          320               325               330

FIG. 2B

Glu Val Gln Ser Ala Leu His Ser Glu Ile Thr Gly Ala Val Asn
           335                 340                 345

Pro Gly Ser Tyr Ala His Leu Gln Ala Thr Ala Leu Ser Gln Leu
           350                 355                 360

Pro Leu Leu Lys Ala Val Ile Lys Glu Val Leu Arg Leu Tyr Pro
           365                 370                 375

Val Val Pro Gly Asn Ser Arg Val Pro Asp Arg Asp Ile Cys Val
           380                 385                 390

Gly Asn Tyr Val Ile Pro Gln Asp Thr Leu Val Ser Leu Cys His
           395                 400                 405

Tyr Ala Thr Ser Arg Asp Pro Ala Gln Phe Arg Glu Pro Asn Ser
           410                 415                 420

Phe Asn Pro Ala Arg Trp Leu Gly Glu Gly Pro Ala Pro His Pro
           425                 430                 435

FIG. 2C

Phe Ala Ser Leu Pro Phe Gly Phe Gly Lys Arg Ser Cys Ile Gly
         440                    445                      450

Arg Arg Leu Ala Glu Leu Glu Leu Gln Met Ala Leu Ala Gln Ile
         455                    460                      465

Leu Thr His Phe Glu Val Leu Pro Glu Pro Gly Ala Leu Pro Val
         470                    475                      480

Lys Pro Met Thr Arg Thr Val Leu Val Pro Glu Arg Ser Ile His
         485                    490                      495

Leu Gln Phe Val Asp Arg
         500

FIG. 2D

CACGAGCTCA AACATGACCC AGGCAGTCAA GCTCGCCTCC AGAGTCTTCC ATCGAGTCCA 60

ACTGCCTTCT CAGCTGGGCA GTGACTCGGT TCTCCGGAGT TTATCTGATA TCCCTGGGCC 120

CTCTACACTT AGCTTCCTGG CTGAACTCTT CTGCAAAGGG GGGCTGTCCA GGCTACATGA 180

ACTGCAGGTG CATGGCGCTG CGCGGTACGG GCCAATATGG TCCGGCAGCT TCGGGACACT 240

TCGCACAGTT TATGTGGCCG ACCCTGCACT TGTAGAGCAG CTCCTGCGAC AAGAAAGTCA 300

TTGTCCAGAG CGCTGTAGTT TCTCATCTTG GTCAGAGCAC CGTCGCCGCC ACCAGCGGGC 360

TTGCGGGTTG CTAACGGCGG ATGGTGAAGA ATGGCAGAGG CTCCGAAGTC TCCTGGCCCC 320

GCATCTCCTC CGACCTCAAG CAGCCGCCGG CTATGCTGGA ACTCTGGACA GCGTGGTCAG 480

TGACCTCGTG CGACGACTAA GGCGCCAGCG GGACGTGGC TCTGGGCTAC CGGACCTAGT 540

TCTGGACGTG GCAGGAGAGT TTTACAAATT TGGCCTAGAA GGCATAGGCG CGGTGCTGCT 600

GGGATCGCGC CTGGGCTGCC TGGAGGCTGA AGTTCCTCCC GACACAGAAA CCTTCATTGA 660

GGCCGTGGGC TCGGTGTTTG TGTCTACACT CTTGACCATG GCAATGCCCA GTTGGCTGCA 720

CCGCCTTATA CCCGGACCCT GGGCCCGCCT CTGCAGAGAC TGGAATCAGA TGTTTGCCTT 780

TGCCCAGAAG CACGTGGAGC AGCGCGAAGG CGAAGCTGCC GTGAGGAACC AGGGAAAGCC 840

TGAGGAGGAT TTGCCAACGG GGCATCACTT AACCCACTTC CTTTTTCGGG AAAAGGTGTC 900

TGTCCAGTCC ATAGTGGGAA ATGTGACAGA GCTACTACTG GCTGGAGTGG ACACGGTATC 960

CAATACGCTC TCCTGGGCAC TCTATGAGCT TTCCCGGCAC CCCGATGTCC AGACTGCACT 1020

CCACTCTGAG ATCACAGCTG GGACCCGTGG CTCCTGTGCC CACCCCCATG GCACTGCACT 1080

GTCCCAGCTG CCCCTGTTAA AGGCTGTGAT CAAAGAAGTG TTGAGATTGT ACCCTGTGGT 1140

ACCTGGGAAT TCCCGTGTCC CAGACAGAGA CATCCGTGTA GGAAACTATG TAATTCCCCA 1200

FIG. 3A

```
AGATACGCTA GTCTCCCTAT GTCACTATGC CACTTCAAGG GACCCCACAC AGTTTCCAGA 1260

CCCCAACTCT TTTAATCCAG CTCGCTGGCT GGGGGAGGGT CCGACCCCCC ACCCATTTGC 1320

ATCTCTTCCC TTCGGCTTTG GCAAACGGAG CTGCATCGGG AGACGCTTGG CAGAGCTTGA 1380

GCTACAAATG GCTTTGTCCC AGATCTTGAC CCATTTTGAA GTGCTACCTG AGCCAGGTGC 1440

TCTTCCTATC AAACCCATGA CCCGGACTG                                  1469
```

FIG. 3B

HUMAN EXON 58-

```
ttggcgtggg cacaggtcaa gtccccgccc agggtatcca agtgtccgct gtgtccgctc        60
ccccagGTGC AGGGCGCCGC GCACTTCGGG CCGGTGTGGC TAGCCAGCTT TGGGACAGTG       120

CGCACCGTGT TACGTGGCTG CCCCTGCACT CGTCGAAGAA CTGCTGCGAC ANGAAGGAAC       180

CCNGGCCGAA CGCTGCAGCT TCTCGCCCTG GAANGAGCGC GCCGCTGCCG CCAGCGGCTT       240

GCGACTGCTC ATGCTTA                                                     257
```

HUMAN EXON 785-957

```
agtattcacg tgcttttac caacgcagTT CAGAGGCACG TGGAGCGGCG AGAGGCAGAG         60

GCAGCCATGA GGAACGGAGG ACAGCCNGAG AAGGACTTGG AGTCTGGGGC GCACCTGACC      120

CAATTCNTGT TCCGGGAAGA GTTGCCTGCC CAGTCCATCC TGGGAAATGT GACAGAGTTG      180

CTATTGGCGG GAGTGGACAC Ggtgaggttc tccctccgtg ctgtgagccg gttccagggc      240
ttagcctccg cagactccgg ctccattttt ctgttgcagg ggatccatta tggccacgta      300
gaccagcttg gcttagcacc ctgtagcccc agactcttcc ataatctgca ccctctgctg      360
ggttctcaca cccaacacct ctcttgcttt cacatgtttt tcag                       404
```

HUMAN EXON 958-1130

```
GTGTCCAACA CGCTCTCTTG GGCTCTGTAT GAGCTCTCCC GGCACCCCGA AGTCCAGACA       60

GCACTCCACT CAGAGATCAC AGCTGCCCTG AGCCCTGGCT CCAGTGCCTA CCCCTCAGCC     120

ACTGTTCTGT CCCAGCTGCC CCTGCTGAAG GCGGTGGTCA AGGAAGTGCT AAGgtgaggg     180
ggaaggagag gaggaacaag angaaatgcc aaggaagggc tgggga                    226
```

FIG. 4A

HUMAN EXON 1131-1207

| | |
|---|---|
| gtgaggggga aggagaggag gaacaagagg aaatgccaag gaagggctgg ggaagcaact | 60 |
| agtggatgga agcagggaga tagcagagaa aaatggccct ctactcctgg ccaaaaaggg | 120 |
| tttggaagtt ggaaacaatg agaaggggc tgcagctagc ctcatcttgt tgtctccatt | 180 |
| ttgtgctttg caacctagAC TGTACCCTGT GGTACCTGGA AATTCTCGTG TCCCAGACAA | 240 |
| AGACATTCAT GTGGGTGACT ATATTATCCC AAAATgtgag taaa | 284 |

HUMAN EXON 1408-1840

| | |
|---|---|
| tttcatagta atgctcacct tcttcccttt ccagATCCTA ACACATTTTG AGGTGCAGCC | 60 |
| TGAGCCAGGT GCGGCCCCAG TTAGACCCAA GACCCGGACT GTCNTGGTAC CTGAAAGGAG | 120 |
| CATCAACCTA CAGTTTTTGG ACAGATAGTC CCATGGAAAG AGACTGTCAT CATCACCCTT | 180 |
| TCATTCATCA TAGGGATAAG ATTTTTTGTA GGCACAAGAC CAAGGTATAC ATCTTCCCCT | 240 |
| AATGCCTATC TGACCAAACT GGATAGAACC ACCATAGTGA AGTGTGAGGC GGCCCTGACC | 300 |
| AATGTGTGAA GTATGCACTT GGCCTGACTC AGGAAGCCAG GTGAGAAAAC CATGGTCTCT | 360 |
| CTGCTTGCTT GGCCCTTCTG ATCATGTATG CATCCCCCAA GGATGAAATC AGATTTTAAC | 420 |
| TAATAATGCT GGATGGCCTG AGGAAAGATT CAACTGCCTC TCTTTTT | 467 |

FIG. 4B

```
RAT    1410 CCAGATCTTGAC CATTTTGAGGTGCTGCCTGAGCCAGGTGCTCTTTCCAGTCAAACCCAT
HUMAN       CCAGATCTAAAC CATTTGGAGGTGCAGCTTGAGCCCAGGTGGGGCCCCAGTAAAACCCAA

RAT    1470 GACCCGGACTGTCCTGGTACCTGAGAGGAGCCATCCATCTCCAGTTTGTAGACAGATAGTC
HUMAN       GACCNGGACTGTCTTGGTACCTGAAAGGAGCATCAAACTACAGTTTTTGGACAGATAGTC

RAT    1530 CTGTGGAAGGCAGCTGTCATCATCTCTC
HUMAN       CCATGGAAAGAGACTGTCATCATCACCCT
```

FIG. 9

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2444 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 16..1518

(xi) SEQUENCE DESCRIPTION: SEQ ID NO:1:

```
GGCACGAGCA CAAAC ATG ACC CAG GCA GTC AAG CTC GCC TCC AGA GTC TTC        51
              Met Thr Gln Ala Val Lys Leu Ala Ser Arg Val Phe
                1               5                  10

CAT CGA GTC CAA CTG CCT TCT CAG CTG GGC AGT GAC TCG GTT CTC CGG         99
His Arg Val Gln Leu Pro Ser Gln Leu Gly Ser Asp Ser Val Leu Arg
             15                  20                  25

AGT TTA TCT GAT ATC CCT GGG CCC TCT ACA CCT AGC TTC CTG GCT GAA         147
Ser Leu Ser Asp Ile Pro Gly Pro Ser Thr Pro Ser Phe Leu Ala Glu
```

```
                30                    35                    40
CTC TTC TGC AAA GGG GGG CTG TCC AGG CTA CAT GAA CTG CAG GTG CAT    195
Leu Phe Cys Lys Gly Gly Leu Ser Arg Leu His Glu Leu Gln Val His
 45              50                      55                  60

GGC GCT GCG CGG TAC GGG CCA ATA TGG TCC GGC AGC TTC GGG ACA CTT    243
Gly Ala Ala Arg Tyr Gly Pro Ile Trp Ser Gly Ser Phe Gly Thr Leu
                 65                      70                  75

CGC ACA GTT TAT GTG GCC GAC CCT GCA CTT GTA GAG CAG CTC CTG CGA    291
Arg Thr Val Tyr Val Ala Asp Pro Ala Leu Val Glu Gln Leu Leu Arg
                 80                      85                  90

CAA GAA AGT CAT TGT CCA GAG CGC TGT AGT TCT CAT CTT GGT CAG AGC    339
Gln Glu Ser His Cys Pro Glu Arg Cys Ser Ser His Leu Gly Gln Ser
             95                     100                 105

ACC GTC GCC AGC CAC CAG CGG GCT TGC GGG TTG CTA ACG GCG GAT GGT    387
Thr Val Ala Ser His Gln Arg Ala Cys Gly Leu Leu Thr Ala Asp Gly
            110                     115                 120

GAA GAA TGG CAA GAG GCT CCG AAG TCT CCT GGC CCC GCA TCT CCT CCG    435
Glu Glu Trp Gln Glu Ala Pro Lys Ser Pro Gly Pro Ala Ser Pro Pro
125                 130                 135                 140

ACC TCA AGC AGC GCC GGC TAT GCT GGA ACT CTG GAC AGC GTG GTC AGT    483
Thr Ser Ser Ser Ala Gly Tyr Ala Gly Thr Leu Asp Ser Val Val Ser
                145                 150                 155

GAC CTC GTG CGA CGA CTA AGG CGC CAG CGG GGA CGT GGC TCT GGG CTA    531
Asp Leu Val Arg Arg Leu Arg Arg Gln Arg Gly Arg Gly Ser Gly Leu
                160                 165                 170

CCG GAC CTA GTT CTG GAC GTG GCG GGA GAG TTT TAC AAA TTT GGC CTA    579
Pro Asp Leu Val Leu Asp Val Ala Gly Glu Phe Tyr Lys Phe Gly Leu
                175                 180                 185

GAA GGC ATA GGC GCG GTG CTG CTG GGA TCG CGC CTG CGC TGC CTG GAG    627
Glu Gly Ile Gly Ala Val Leu Leu Gly Ser Arg Leu Arg Cys Leu Glu
190                 195                 200

GCT GAA GTT CCT CCC GAC ACA GAA ACC TTC ATT GAG GCC GTG GGC TCG    675
Ala Glu Val Pro Pro Asp Thr Glu Thr Phe Ile Glu Ala Val Gly Ser
205                 210                 215                 220

GTG TTT GTG TCT ACA CTC TTG ACC ATG GCA ATG CCC AGT TGG CTG CAC    723
Val Phe Val Ser Thr Leu Leu Thr Met Ala Met Pro Ser Trp Leu His
                225                 230                 235

CGC CTT ATA CCC GGA CCC TGG GCC CGC CTC TGC AGA GAC TGG AAT CAG    771
Arg Leu Ile Pro Gly Pro Trp Ala Arg Leu Cys Arg Asp Trp Asn Gln
                240                 245                 250

ATG TTT GCC TTT GCC CAG AAG CAC GTG GAG CAG CGC GAA GGC GAA GCT    819
Met Phe Ala Phe Ala Gln Lys His Val Glu Gln Arg Glu Gly Glu Ala
                255                 260                 265

GCC GTG AGG AAC CAG GGA AAG CCT GAG GAG GAT TTG CCA ACG GGG CAT    867
Ala Val Arg Asn Gln Gly Lys Pro Glu Glu Asp Leu Pro Thr Gly His
            270                 275                 280

CAC TTA ACC GAC TTC CTT TTT CGG GAA AAG GTG TCT GTC CAG TCC ATA    915
His Leu Thr Asp Phe Leu Phe Arg Glu Lys Val Ser Val Gln Ser Ile
285                 290                 295                 300

GTG GGA AAT GTG AGA GAG CTA CTA CTG GCT GGA GTG GAC ACG GTA TCC    963
Val Gly Asn Val Arg Glu Leu Leu Leu Ala Gly Val Asp Thr Val Ser
                305                 310                 315

AAT ACG CTC TCC TGG GCA CTC TAT GAG CTC TCC CGG CAC CCG GAA GTC   1011
Asn Thr Leu Ser Trp Ala Leu Tyr Glu Leu Ser Arg His Pro Glu Val
                320                 325                 330

CAG TCT GCA CTC CAC TCT GAG ATC ACA GGC GCT GTG AAC CCT GGC TCC   1059
Gln Ser Ala Leu His Ser Glu Ile Thr Gly Ala Val Asn Pro Gly Ser
                335                 340                 345

TAT GCC CAC CTC CAA GCC ACT GCT CTG TCC CAG CTA CCC CTG CTA AAG   1107
```

```
Tyr Ala His Leu Gln Ala Thr Ala Leu Ser Gln Leu Pro Leu Leu Lys
    350                 355                 360

GCT GTG ATC AAA GAA GTG TTG AGG TTG TAC CCT GTG GTA CCT GGG AAC    1155
Ala Val Ile Lys Glu Val Leu Arg Leu Tyr Pro Val Val Pro Gly Asn
365                 370                 375                 380

TCC CGT GTC CCA GAC AGA GAC ATC TGT GTA GGA AAC TAT GTT ATT CCC    1203
Ser Arg Val Pro Asp Arg Asp Ile Cys Val Gly Asn Tyr Val Ile Pro
                    385                 390                 395

CAA GAT ACA CTG GTT TCC CTC TGT CAC TAT GCC ACT TCA AGG GAC CCC    1251
Gln Asp Thr Leu Val Ser Leu Cys His Tyr Ala Thr Ser Arg Asp Pro
            400                 405                 410

GCC CAG TTT CGG GAA CCC AAC TCT TTT AAT CCA GCT CGA TGG CTT GGA    1299
Ala Gln Phe Arg Glu Pro Asn Ser Phe Asn Pro Ala Arg Trp Leu Gly
        415                 420                 425

GAG GGT CCA GCC CCC CAC CCA TTT GCA TCT CTT CCT TTT GGC TTT GGC    1347
Glu Gly Pro Ala Pro His Pro Phe Ala Ser Leu Pro Phe Gly Phe Gly
    430                 435                 440

AAA CGA AGT TGC ATA GGG AGA CGC TTG GCA GAG CTC GAG CTA CAA ATG    1395
Lys Arg Ser Cys Ile Gly Arg Arg Leu Ala Glu Leu Glu Leu Gln Met
445                 450                 455                 460

GCG TTG GCC CAG ATC TTG ACC CAT TTT GAG GTG CTG CCT GAG CCA GGT    1443
Ala Leu Ala Gln Ile Leu Thr His Phe Glu Val Leu Pro Glu Pro Gly
                465                 470                 475

GCT CTT CCA GTC AAA CCC ATG ACC CGG ACT GTC CTG GTA CCT GAG AGG    1491
Ala Leu Pro Val Lys Pro Met Thr Arg Thr Val Leu Val Pro Glu Arg
            480                 485                 490

AGC ATC CAT CTC CAG TTT GTA GAC AGA TAGTCCTGTG GAAGGCAGCT          1538
Ser Ile His Leu Gln Phe Val Asp Arg
        495                 500

GTCATCATCT CTCTCCAGAC TGGATTTTTC TTACTATGCA CAAGAGGCAC ACTCTCCCTC  1598

GAGGCCTGTC TGTCTGAGCA AACTTCAGGA AGCAGGCCCG GGCCTATCTG TGCTTGACCT  1658

GACTCAGCAG GTACCACAGA ACCAGGATCC TTTCTCCTGC TCAGTACCTC TCCTGATCAT  1718

TCCTCAAGAT CCAAAGCCTT CAGATTTTAA CACATCCTTA AAGGGCCAAC TCGGGGGTTA  1778

ACTAACAGCC CCAGGCAGCC TGGGCAGGGA TCCCCCACTG ATCCTTCCAT GCTTACAGTG  1838

TTCACTGACA GCTGTCTAAG CATCCATTGC AGCACAAACT AAGTGACTGT GCACCTGGTC  1898

TGCACCTGGT CTGCACCTGG TTGCGTCTCT GCCTGACCAT GTGAGCTCTT TGAGAAGAGT  1958

GATGACTACT GGGCTTTTAG CTCTTTTCCT TTTTGGGACA CAGTCTTGCT ATTGTACTCC  2018

ATGCTGTCCT TGAACCCACA AGCCCTCACC TCACCTTCCC AAGTGTTGGG TTACGGACAT  2078

TAGCTATGCC TGCCAGCTTT ATTAGTCTTT CTATCTCCTG CCATGGTCTA TCCCCGGCTA  2138

TTTGATACTA TATATTCTCA GATTGAATCT GGACCATGTG GTAGAAGGGA TGACCACTGA  2198

CCAGGCTCTA CCCACCACTT TATCTTAATC TTTTCTCTAG GAAAGTGAAT CTCTCCTTGC  2258

CTTACAGCAT TTTAAAGCTC CCCTTGGCTG TTCTGCTCTT TAGCCACTCT AAAGTGGATC  2318

CACTCTACTT CTCACCACCC ATCTTTCTGC ACCCCAGCCT GTCTTTTTAT ATTAAAAAAA  2378

TTGTATTTAT TATGTTTTCA AATAAAATGT TTACTCCTTG AAAAAAAAAA AAAAAAAAA   2438

AAAAAA                                                             2444

(2) INFORMATION FOR SEQ ID NO:2:

(i) SEQUENCE CHARACTERISTICS:
        (A) LENGTH: 501 amino acids
        (B) TYPE: amino acid
        (D) TOPOLOGY: linear
```

(ii) MOLECULE TYPE: protein (xi) SEQUENCE DESCRIPTION: SEQ ID NO:2:

```
Met Thr Gln Ala Val Lys Leu Ala Ser Arg Val Phe His Arg Val Gln
 1               5                  10                  15

Leu Pro Ser Gln Leu Gly Ser Asp Ser Val Leu Arg Ser Leu Ser Asp
                20                  25                  30

Ile Pro Gly Pro Ser Thr Pro Ser Phe Leu Ala Glu Leu Phe Cys Lys
            35                  40                  45

Gly Gly Leu Ser Arg Leu His Glu Leu Gln Val His Gly Ala Ala Arg
        50                  55                  60

Tyr Gly Pro Ile Trp Ser Gly Ser Phe Gly Thr Leu Arg Thr Val Tyr
65                  70                  75                  80

Val Ala Asp Pro Ala Leu Val Glu Gln Leu Leu Arg Gln Glu Ser His
                85                  90                  95

Cys Pro Glu Arg Cys Ser Ser His Leu Gly Gln Ser Thr Val Ala Ser
            100                 105                 110

His Gln Arg Ala Cys Gly Leu Leu Thr Ala Asp Gly Glu Glu Trp Gln
        115                 120                 125

Glu Ala Pro Lys Ser Pro Gly Pro Ala Ser Pro Thr Ser Ser Ser
130                 135                 140

Ala Gly Tyr Ala Gly Thr Leu Asp Ser Val Val Ser Asp Leu Val Arg
145                 150                 155                 160

Arg Leu Arg Arg Gln Arg Gly Arg Gly Ser Gly Leu Pro Asp Leu Val
                165                 170                 175

Leu Asp Val Ala Gly Glu Phe Tyr Lys Phe Gly Leu Glu Gly Ile Gly
            180                 185                 190

Ala Val Leu Leu Gly Ser Arg Leu Arg Cys Leu Glu Ala Glu Val Pro
        195                 200                 205

Pro Asp Thr Glu Thr Phe Ile Glu Ala Val Gly Ser Val Phe Val Ser
            210                 215                 220

Thr Leu Leu Thr Met Ala Met Pro Ser Trp Leu His Arg Leu Ile Pro
225                 230                 235                 240

Gly Pro Trp Ala Arg Leu Cys Arg Asp Trp Asn Gln Met Phe Ala Phe
                245                 250                 255

Ala Gln Lys His Val Glu Gln Arg Glu Gly Glu Ala Ala Val Arg Asn
            260                 265                 270

Gln Gly Lys Pro Glu Glu Asp Leu Pro Thr Gly His His Leu Thr Asp
        275                 280                 285

Phe Leu Phe Arg Glu Lys Val Ser Val Gln Ser Ile Val Gly Asn Val
290                 295                 300

Arg Glu Leu Leu Leu Ala Gly Val Asp Thr Val Ser Asn Thr Leu Ser
305                 310                 315                 320

Trp Ala Leu Tyr Glu Leu Ser Arg His Pro Glu Val Gln Ser Ala Leu
                325                 330                 335

His Ser Glu Ile Thr Gly Ala Val Asn Pro Gly Ser Tyr Ala His Leu
            340                 345                 350

Gln Ala Thr Ala Leu Ser Gln Leu Pro Leu Leu Lys Ala Val Ile Lys
        355                 360                 365

Glu Val Leu Arg Leu Tyr Pro Val Pro Gly Asn Ser Arg Val Pro
            370                 375                 380

Asp Arg Asp Ile Cys Val Gly Asn Tyr Val Ile Pro Gln Asp Thr Leu
385                 390                 395                 400
```

```
Val Ser Leu Cys His Tyr Ala Thr Ser Arg Asp Pro Ala Gln Phe Arg
            405                 410                 415

Glu Pro Asn Ser Phe Asn Pro Ala Arg Trp Leu Gly Glu Gly Pro Ala
            420                 425                 430

Pro His Pro Phe Ala Ser Leu Pro Phe Gly Phe Gly Lys Arg Ser Cys
            435                 440                 445

Ile Gly Arg Arg Leu Ala Glu Leu Glu Leu Gln Met Ala Leu Ala Gln
    450                 455                 460

Ile Leu Thr His Phe Glu Val Leu Pro Glu Pro Gly Ala Leu Pro Val
465                 470                 475                 480

Lys Pro Met Thr Arg Thr Val Leu Val Pro Glu Arg Ser Ile His Leu
                485                 490                 495

Gln Phe Val Asp Arg
            500
```

(2) INFORMATION FOR SEQ ID NO:3:

(i) SEQUENCE CHARACTERISTICS:
        (A) LENGTH: 1469 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

```
CACGAGCTCA AACATGACCC AGGCAGTCAA GCTCGCCTCC AGAGTCTTCC ATCGAGTCCA      60

ACTGCCTTCT CAGCTGGGCA GTGACTCGGT TCTCCGGAGT TTATCTGATA TCCCTGGGCC     120

CTCTACACTT AGCTTCCTGG CTGAACTCTT CTGCAAAGGG GGGCTGTCCA GGCTACATGA     180

ACTGCAGGTG CATGGCGCTG CGCGGTACGG GCCAATATGG TCCGGCAGCT TCGGGACACT     240

TCGCACAGTT TATGTGGCCG ACCCTGCACT TGTAGAGCAG CTCCTGCGAC AAGAAAGTCA     300

TTGTCCAGAG CGCTGTAGTT TCTCATCTTG GTCAGAGCAC CGTCGCCGCC ACCAGCGGGC     360

TTGCGGGTTG CTAACGGCGG ATGGTGAAGA ATGGCAGAGG CTCCGAAGTC TCCTGGCCCC     420

GCATCTCCTC CGACCTCAAG CAGCCGCCGG CTATGCTGGA ACTCTGGACA GCGTGGTCAG     480

TGACCTCGTG CGACGACTAA GGCGCCAGCG GGACGTGGC  TCTGGGCTAC CGGACCTAGT     540

TCTGGACGTG GCAGGAGAGT TTTACAAATT TGGCCTAGAA GGCATAGGCG CGGTGCTGCT     600

GGGATCGCGC CTGGGCTGCC TGGAGGCTGA AGTTCCTCCC GACACAGAAA CCTTCATTGA     660

GGCCGTGGGC TCGGTGTTTG TGTCTACACT CTTGACCATG GCAATGCCCA GTTGGCTGCA     720

CCGCCTTATA CCCGGACCCT GGGCCCGCCT CTGCAGAGAC TGGAATCAGA TGTTTGCCTT     780

TGCCCAGAAG CACGTGGAGC AGCGCGAAGG CGAAGCTGCC GTGAGGAACC AGGGAAAGCC     840

TGAGGAGGAT TGCCAACGG  GGCATCACTT AACCCACTTC CTTTTTCGGG AAAAGGTGTC     900

TGTCCAGTCC ATAGTGGGAA ATGTGACAGA GCTACTACTG GCTGGAGTGG ACACGGTATC     960

CAATACGCTC TCCTGGGCAC TCTATGAGCT TTCCCGGCAC CCCGATGTCC AGACTGCACT    1020

CCACTCTGAG ATCACAGCTG GGACCCGTGG CTCCTGTGCC CACCCCCATG GCACTGCACT    1080

GTCCCAGCTG CCCCTGTTAA AGGCTGTGAT CAAAGAAGTG TTGAGATTGT ACCCTGTGGT    1140

ACCTGGGAAT TCCCGTGTCC CAGACAGAGA CATCCGTGTA GGAAACTATG TAATTCCCCA    1200

AGATACGCTA GTCTCCCTAT GTCACTATGC CACTTCAAGG GACCCCACAC AGTTTCCAGA    1260
```

```
CCCCAACTCT TTTAATCCAG CTCGCTGGCT GGGGGAGGGT CCGACCCCCC ACCCATTTGC      1320

ATCTCTTCCC TTCGGCTTTG GCAAACGGAG CTGCATCGGG AGACGCTTGG CAGAGCTTGA      1380

GCTACAAATG GCTTTGTCCC AGATCTTGAC CCATTTTGAA GTGCTACCTG AGCCAGGTGC      1440

TCTTCCTATC AAACCCATGA CCCGGACTG                                        1469
```

(2) INFORMATION FOR SEQ ID NO:4:

(i) SEQUENCE CHARACTERISTICS:
        (A) LENGTH: 257 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
TTGGCGTGGG CACAGGTCAA GTCCCCGCCC AGGGTATCCA AGTGTCCGCT GTGTCCGCTC        60

CCCCAGGTGC AGGGCGCCGC GCACTTCGGG CCGGTGTGGC TAGCCAGCTT TGGGACAGTG       120

CGCACCGTGT TACGTGGCTG CCCCTGCACT CGTCGAAGAA CTGCTGCGAC ANGAAGGAAC       180

CCNGGCCGAA CGCTGCAGCT TCTCGCCCTG GAANGAGCGC GCCGCTGCCG CCAGCGGCTT       240

GCGACTGCTC ATGCTTA                                                      257
```

(2) INFORMATION FOR SEQ ID NO:5:

(i) SEQUENCE CHARACTERISTICS:
        (A) LENGTH: 404 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

```
AGTATTCACG TGCTTTTTAC CAACGCAGTT CAGAGGCACG TGGAGCGGCG AGAGGCAGAG        60

GCAGCCATGA GGAACGGAGG ACAGCCNGAG AAGGACTTGG AGTCTGGGGC GCACCTGACC       120

CAATTCNTGT TCCGGGAAGA GTTGCCTGCC CAGTCCATCC TGGGAAATGT GACAGAGTTG       180

CTATTGGCGG GAGTGGACAC GGTGAGGTTC TCCCTCCGTG CTGTGAGCCG GTTCCAGGGC       240

TTAGCCTCCG CAGACTCCGG CTCCATTTTT CTGTTGCAGG GGATCCATTA TGGCCACGTA       300

GACCAGCTTG GCTTAGCACC CTGTAGCCCC AGACTCTTCC ATAATCTGCA CCCTCTGCTG       360

GGTTCTCACA CCCAACACCT CTCTTGCTTT CACATGTTTT TCAG                        404
```

(2) INFORMATION FOR SEQ ID NO:6:

(i) SEQUENCE CHARACTERISTICS:
        (A) LENGTH: 226 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

GTGTCCAACA CGCTCTCTTG GGCTCTGTAT GAGCTCTCCC GGCACCCCGA AGTCCAGACA     60

GCACTCCACT CAGAGATCAC AGCTGCCCTG AGCCCTGGCT CCAGTGCCTA CCCCTCAGCC    120

ACTGTTCTGT CCCAGCTGCC CCTGCTGAAG GCGGTGGTCA AGGAAGTGCT AAGGTGAGGG    180

GGAAGGAGAG GAGGAACAAG ANGAAATGCC AAGGAAGGGC TGGGGA                  226

(2) INFORMATION FOR SEQ ID NO:7:

(i) SEQUENCE CHARACTERISTICS:
        (A) LENGTH: 284 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

GTGAGGGGGA AGGAGAGGAG GAACAAGAGG AAATGCCAAG GAAGGGCTGG GGAAGCAACT     60

AGTGGATGGA AGCAGGGAGA TAGCAGAGAA AAATGGCCCT CTACTCCTGG CCAAAAAGGG    120

TTTGGAAGTT GGAAACAATG AGAAGGGGGC TGCAGCTAGC CTCATCTTGT TGTCTCCATT    180

TTGTGCTTTG CAACCTAGAC TGTACCCTGT GGTACCTGGA AATTCTCGTG TCCCAGACAA    240

AGACATTCAT GTGGGTGACT ATATTATCCC AAAATGTGAG TAAA                    284

(2) INFORMATION FOR SEQ ID NO:8:

(i) SEQUENCE CHARACTERISTICS:
        (A) LENGTH: 467 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

TTTCATAGTA ATGCTCACCT TCTTCCCTTT CCAGATCCTA ACACATTTTG AGGTGCAGCC     60

TGAGCCAGGT GCGGCCCCAG TTAGACCCAA GACCCGGACT GTCNTGGTAC CTGAAAGGAG    120

CATCAACCTA CAGTTTTTGG ACAGATAGTC CCATGGAAAG AGACTGTCAT CATCACCCTT    180

TCATTCATCA TAGGGATAAG ATTTTTTGTA GGCACAAGAC CAAGGTATAC ATCTTCCCCT    240

AATGCCTATC TGACCAAACT GGATAGAACC ACCATAGTGA AGTGTGAGGC GGCCCTGACC    300

AATGTGTGAA GTATGCACTT GGCCTGACTC AGGAAGCCAG GTGAGAAAAC CATGGTCTCT    360

CTGCTTGCTT GGCCCTTCTG ATCATGTATG CATCCCCCAA GGATGAAATC AGATTTTAAC    420

TAATAATGCT GGATGGCCTG AGGAAAGATT CAACTGCCTC TCTTTTT                 467

1-α-HYDROXYLASE MATERIALS AND METHODS

FIELD OF THE INVENTION

This invention relates to polynucleotide molecules encoding 25-hydroxyvitamin D 1-α-hydroxylase and polypeptides encoded thereby.

BACKGROUND OF THE INVENTION

Vitamin D is a hormone involved in calcium absorption from the gut and mobilization of calcium from bone. Before it can function as a hormone, vitamin D undergoes two separate hydroxylation steps. It is first hydroxylated in the liver, at carbon 25, to generate a biologically inactive metabolite, 25-hydroxyvitamin D (25(OH)D), by the enzyme vitamin D 25-hydroxylase (25-OHase). 25(OH)D is further hydroxylated by mitochondria in the kidney to one of two metabolites: $1\alpha,25$-dihydroxyvitamin $D_3$ ($1\alpha,25(OH)_2D_3$), the active form of the vitamin, and $24R,25$-dihydroxyvitamin $D_3$.

The conversion of 25(OH)D to 24R,25-dihydroxyvitamin $D_3$ is catalyzed by the enzyme 25-hydroxyvitamin $D_3$ 24-hydroxylase (24-OHase). The enzyme has been cloned and its cDNA expressed by Ohyama et al., FEBS Lett, 278: 195–198 (1991). The conversion of 25(OH)D to $1\alpha,25(OH)_2D_3$ is catalyzed by 25-hydroxyvitamin D-1α-hydroxylase, a renal cytochrome P450 enzyme of the vitamin D pathway (hereinafter referred to as 1α-OHase).

Expression of 1α-OHase activity is under tight hormonal control. 1α-OHase activity is stimulated in mammalian cell culture systems by parathyroid hormone (PTH), while $1\alpha,25(OH)_2D_3$ represses it (Trechsel et al, FEBS Lett. 1.35:115–118 (1981); Henry, J., Biol Chem 254: 2722–2729 (1979)). These regulatory responses are rapid and have been demonstrated to require de novo mRNA synthesis (Turner, *Vitamin D; Basic and Clinical Aspects*, Kumar, R. ed. (The Hague: Martinus Nijhoff: 1984)) indicating that they may occur at the transcriptional level.

Abnormalities in any step of vitamin D metabolism, from dietary deficiency through metabolic errors to end-organ resistance (i.e. mutations of the receptor for $1\alpha,25(OH)_2D_3$) can result in rickets or osteomalacia. The first identified inborn defect in vitamin D metabolism was pseudovitamin D-deficiency rickets (PDDR). PDDR is an autosomal recessive disorder characterized at the biochemical level by low serum calcium, secondary hyperparathyroidism and early onset of rickets. PDDR appears to be caused by impaired activity of 1α-OHase.

The disease locus for PDDR was mapped by linkage analysis to 12q13-q14 by Labuda et al, Am J. Hum. Genet. 47:28–36 (1990), but the molecular defect underlying the enzyme dysfunction has remained elusive owing to the lack of sequence information for the gene coding for 1α-OHase and the consequent inability to produce clones of the gene.

Accordingly, a need exists for determination of the sequence of the polynucleotide coding for 1α-OHase and for clones of the 1α OHase cDNA.

SUMMARY OF THE INVENTION

The present invention relates to polynucleotide sequences coding for 1α-OHase and fragments thereof in rats, mice and humans.

The present invention further relates to polypeptides encoded by polynucleotide sequences coding for 1α-OHase and fragments thereof in rats, mice and humans.

The present invention also relates to a method for diagnosing bone, skin, kidney, endocrine or neoplastic diseases using the polynucleotides and polypeptides of the invention.

The present invention also relates to a method for treating Vitamin D-related disorders including bone, skin, kidney, endocrine or neoplastic diseases by administering the polynucleotides or polypeptides of the invention to a patient.

The present invention further relates to the production of vitamin D metabolites using the polynucleotides of the invention.

The present invention further relates to the production and use of antibodies produced using the proteins and peptides of the subject invention.

The polynucleotides, polypeptides and antibodies of the subject invention have application in the study of vitamin D metabolism, in the production of vitamin D metabolites, in diagnostic assays and in therapeutic protocols.

BRIEF DESCRIPTION OF THE DRAWINGS

FIG. 1 shows the sequence of the rat 1α-OHase cDNA (SEQ ID NO:1).

FIG. 2 shows the deduced amino acid sequence of the rat 1α-OHase protein (SEQ ID NO:2).

FIG. 3 shows the sequence of the mouse 1α-OHase cDNA (SEQ ID NO:3).

FIG. 4 shows the sequence of exons for partial sequences of the human 1α-OHase gene (SEQ ID NOS:4–8).

FIG. 9 shows an alignment of a partial human 1α-OHase genomic sequence to the rat 1α-OHase cDNA.

DETAILED DESCRIPTION

Figure 5:
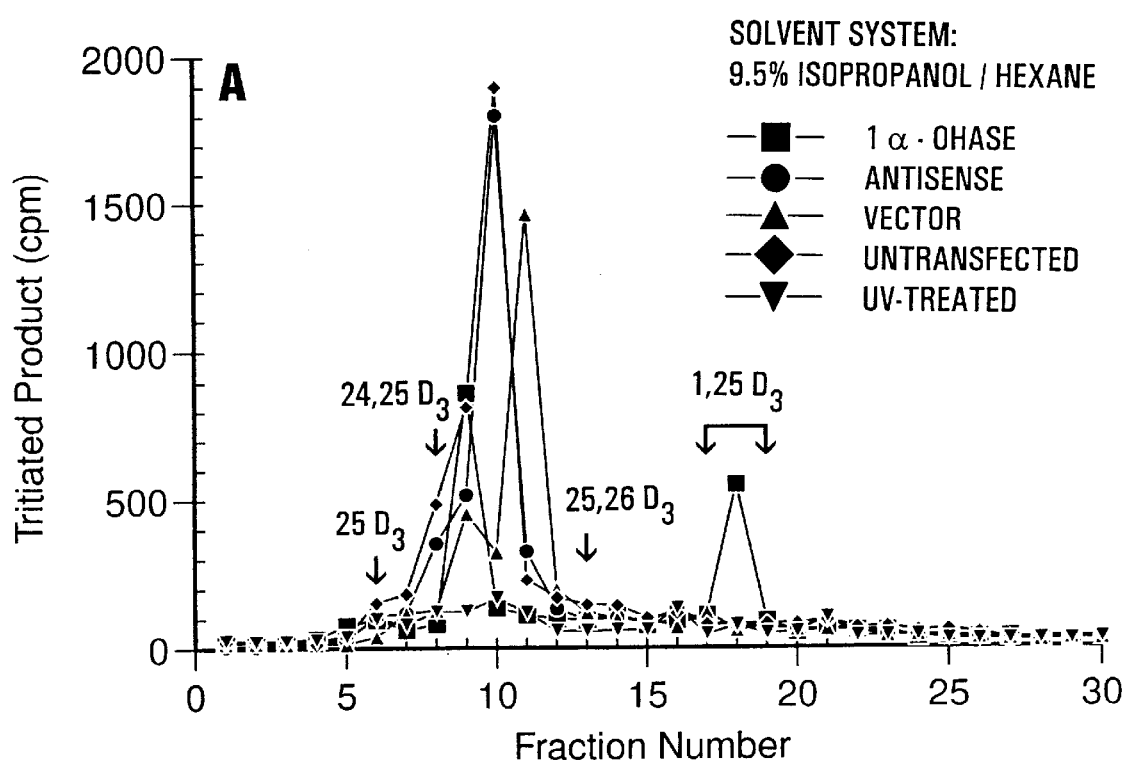
FIG. 5 shows an HPLC elution profile of extracts from P19 embryonal carcinoma cells transiently transfected with control or 1α-OHase expression vectors eluted with 9.5% isopropanol.

Applicant has cloned a full length cDNA encoding the P450 moiety of the rat 1α-OHase enzyme. The sequence is shown in FIG. 1 (SEQ ID NO:2). The deduced sequence of the protein encoded by the rat 1α-OHase gene is shown in FIG. 2.

In addition to the cDNA from rat, applicant has also cloned a full length cDNA encoding the P450 moiety of the 1α-OHase enzyme from mouse, shown in FIG. 3 (SEQ ID NO:3).

Applicant has cloned a partial sequence of thee corresponding human gene, shown in FIG. 9 in alignment with the cDNA from rat.

Functional expression studies were conducted on the cDNA from rat which indicated that the only enzymatic activity of the clone was 1α-hydroxylation.

Comparison of the 1α-OHase sequence with other cytochrome P450 enzymes involved in vitamin D metabolism revealed overall homology of 26% and 36% with 24-OHase and 25-OHase respectively. Nebert et al, Ann. Rev. Biochem. 56: 945–993 (1987), classified each cytochrome P450 family based on an overall 36% homology between given families. Using this estimate, the 1α-OHase may constitute a novel P450 family or may be considered to belong to the same family as the 25-OHase.

The rat cDNA was used to convert tritiated substrate to $1\alpha,25(OH)_2D_3$. A level of conversion was obtained of about 1%. This level is comparable to the level of conversion in primary cultures of kidney cells, where it ranges from 3–12%, as observed by Trechlsel et al. J Clin Invest 64: 206–217 (1979) and Trechsel and Fleisch FEBS Lett. 135: 11–118 (1981). Considering the variable efficiency of transient transfection assays, the observed difference in conversion rates appears marginal and further suggests that the enzymatic reaction was efficient and specifically due to the expression of the cloned sequence.

The 1α-OHase gene was mapped to 12q13.1–q13.3, which closely corresponds to the chromosomal location of the disease locus for PDDR. This provides strong evidence that an alteration of the 1α-OHase gene is responsible for the PDDR phenotype.

The polynucleotide sequences of the subject invention include all or a portion of the polynucleotide molecules coding for the 1α-OHase gene in rat, mouse and human as well as the specific polypeptides shown in FIGS. 1,3,4 and 9. Encompassed within the scope of the invention are polynucleotide sequences composed of DNA and their complementary RNA sequences. It will also be understood by those of skill in the art that the subject invention is not limited to the exact sequence of the polynucleotides as shown in the figures but includes variants, including allelic variations or polymorphisms of the 1α-OHase sequence.

The subject invention also encompasses those polynucleotide sequences which are sufficiently similar in nucleotide sequence to all or a portion of the sequences shown in the figures such that they can hybridize with all or a portion of the sequences shown under standard medium to high-stringency conditions. Hybridization stringency conditions, including medium and high stringency, can be selected and used according to the method described by Sambrook et al. *Molecular Cloning: a Laboratory Manual* 2nd ed.(Cold Spring Harbor: Cold Spring Harbor Laboratory Press, 1989). In particular, within the scope of the invention are polynucleotide molecules of the complete human homolog of the 1α-OHase gene. Human cDNAs or human genomic fragments that hybridize with the 1α-OHase molecules described herein can be readily isolated from a human cDNA or genomic library using standard methods known in the art. These polynucleotides cal also be used to express the human 1α-OHase polypeptide.

As is well known in the art, the genetic code is redundant in that certain amino acids are coded for by more than one nucleotide triplet (codon). The subject invention includes those polynucleotide sequences which encode the same amino acids using different nucleotides from those specifically exemplified in the figures. Thus, the scope of the subject invention includes not only the specific polynucleotide sequences depicted herein, but also all equivalent polynucleotide sequences encoding the polypeptidets of the subject invention, and fragments or variants of the polypeptides having the same activity.

The polynucleotide sequences of the subject invention can be prepared according to the teachings contained herein, or by synthesis of oligonucleotide fragments, for example by using a "gene machine" using procedures well known in the art.

The polypeptides of the subject invention can be prepared by expression of the polynucleotide sequences in a compatible host cell using an expression vector containing the polynucleotide sequences of the subject invention. The cloning or expression vector may be of bacterial or viral origin. The host cell may be either prokaryotic or eukaryotic and includes bacteria, yeast, insect cells and mammalian cells. The polypeptides can then be purified from the host cell using standard purification techniques that are well known in the art. Alternatively, the polypeptides of the subject invention can be chemically synthesized using solid phase peptide synthesis tecluiiques known in the art.

Polynucleotide molecules that are anti-sense to the RNA of 1α-OHase can be prepared using techniques which are known in the art. For example, anti-sense polynucleotide molecules can be encapsulated into liposomes for fusion with cells. Anti-sense polynucleotide molecules can be used to reduce or inhibit the expression of the subject protein by binding to the complementary mRNA transcripts. Administration of an anti-sense polynucleotide molecule to a patient can block the production of the protein encoded by the 1α-OHase polyaucleotide described herein or a related, possibly defective gene.

The protein and peptides of the subject invention can be used to generate both polyclonal and monoclonal antibodies using techniques well known to those of skill in the art. Specifically, polyclonal antibodies can be raised in animal systems. Monoclonal antibodies can be prepared using hybridoma technology. Antibodies raised against the 1α-OHase polypeptide or synthetic peptides thereof are within the scope of the invention.

The polynucleotides and polypeptides of the present invention can be used for enzymatic production of vitamin D metabolites. In addition, they can be used to clinical diagnosis of bone, skin, kidney, endocrine or neoplastic diseases. For example, polynucleotide sequences of the 1α-OHase can be employed as probes to study the expression of the 1α-OHase gene or to identify or diagnose rickets.

The antibodies of the subject invention can be used in assays to identify or quantify the amount of 1α-OHase present in a sample. The antibodies can also be used for purification of the subject polypeptide.

The molecules of the subject invention can also be used to treat patients that are afflicted with bone, skin, kidney, endocrine and/or neoplastic diseases using gene therapy protocols. For example, the polynucleotide sequences of the present invention can be incorporated into vectors that are suitable for delivering the subject polynucleotide sequences into the cells of a patient afflicted with such diseases, for example PDDR or renal failure. The sequences are inserted and expressed in the patient's cells such that the patient's transformed cells will produce the polypeptide encoded by the polynucleotide sequence.

The polynucleotide sequences of the subject invention can also be used in anti-sense gene therapy protocols. For anti-sense therapy, a polynucleotide sequence of the present invention is selected which encodes an anti-sense polynucleotide strand, typically RNA, which is capable of binding to an RNA sense strand. Anti-sense therapy is directed to preventing the production of defective proteins in the patient's cells through the annealing of an anti-sense strand to the RNA sense strand. Gene therapy protocols are known to those skilled in the art.

The following examples are provided in order to illustrate the methods of the present invention and are not meant to limit the scope of the invention.

EXAMPLE 1

Cloning of the Rat 1α-OHase cDNA

Since the 1α-OHase and 24-OHase are both cytochrome P450 mixed function monooxydases and utilize the same substrate, namely 25-hydroxyvitamin D [25(OH)D], it is possible that they have some degree of similarity. A probe was used which was derived from the 3'-region of the rat 24-OHase cDNA using the protocol described by Ohyama et al. FEBS Lett. 273:195–198 (1991). It encompassed the heme-binding domain of the molecule. A cDNA library was constructed from kidney mRNA of vitamin D-deficient animals in order to reduce the possibility that the probe would identify the parental 24-OHase cDNA. Expression of the 24-OHase transcript is undetectable in vitamin D-deprived rats. Kidneys from six week old Sprague-Dawley rats fed a vitamin D-deficient diet (0.47% calcium, 0.3% phosphorus, vitamin D-depleted) ad libitum from 10 days of age were used to isolate poly-A+ mRNA according to the method described by Arabian et al, J. Steriod Biochem Molec. Biol 45:513–516 (1993). The extraction and isolation was performed using the Poly ATract System 1000 kit (Promega Corp., Madison Wis.) according to the manufacturer's instructions. The mRNA was then used with the ZAP-cDNA Synthesis kit (Stratagene; LaJolla, Calif.) for construction of the kidney cDNA library. A Hinc II-to-Kpn I 263 bp fragment containing the heme binding domain of the 24-OHase cDNA fragment was isolated, labelled and used as a probe to screen the cDNA library by plaque hybridization at low stringency. Hybridization was for 20 h in 5× SSC, 15% formamide, 5× Denhardt'solution, 1% SDS, 10mM EDTA and 100 mg/ml of heat denatured salmon sperm DNA at 44° C. Filters were washed 2×10 min at room temperature in 2× SSC/0.1% SDS, and 2×20 min at 37° C. in 1× SSC/0.1% SDS. Positive clones were plaque-purified and phage DNA was isolated by in vivo excision using the Exassist/SOLR kit (Stratagene; Lajolla, Calif.) as per the recommended protocol. The 1α-OHase cDNA was sequenced using the dideoxy chain termination method with the 7-deaza dGTP Sequenase kit (United States Biochemical-Amersham Life Science; Oakville, ON). Sequence data was assembled and analysed using the Mac-Molly Tetra software (Soft Gene GmbH: Berlin Germany).

FIG. 1 shows the complete sequence of the rat 1α-OHase clone, 2424 base pairs in length, revealing an open reading frame of 1503 base pairs and coding for a 501 amino acid protein (Mr ~55 kD) shown in FIG. 2. A heme-binding region as described in Nebert et al. Ann. Rev. Biochem. 56: 945–993 (1987) is observed between residues 441 and 462. Amino acid sequence identity with the 24-OHase enzyme was calculated as 76% within the heme binding domain. The two proteins diverged significantly outside of this region for an overall sequence similarity of 26%. Comparison with the rat 25-OHase cDNA sequence revealed a 67% sequence similarity in the heme region, but an overall sequence similarity of 36%. Further sequence comparisons with current DNA databases confirmed that the clone is a novel cytochrome P450 cDNA.

EXAMPLE 2

Expression of the Cloned Sequence

The 1α-OHase cDNA was transiently expressed in embryonal carcinoma cells in the following manner. The full-length 1α-OHase cDNA was subcloned downstream of the cytomegalovirus (CMV) promoter of the pCI mammalian expression vector (Promega Corp.) in both the sense and antisense orientation. P19 enbryonal carcinoma cells as described by McBurney, Int. J. Dev. Biol. 37: 135–140 (1993), were transfected with 6 μg of the 1α-OHase expression vector using 15 μl of Lipofectamine™ Reagent (Gibco BRL, Canadian Life Technologies, Burlington ON) in PBS for 8 h. Twenty-four hours post-transefection, the cells were incubated for 8 h in serum-free αMEM supplemented with 50 nM of 25-hydroxy-[26,27-methyl-3H] vitamin $D_3$ (10 Ci/mmol; Amersham Lite Science, Oakville ON). Cells and media were harvested and extracted twice each with 10 ml of anhydrous diethylether. Organic phases were collected, pooled and evaporated to dryness in a 37° C. water bath under a stream of nitrogen. Samples were redissolved in 45% diethylether in hexane and purified by column chromatography using the method described by Delvin et al, Eur. J. Biochem 163: 659–662 (1987). The purified fractions were resuspended in 100 μl of 9.5% isopropanol in hexane. High pressure liquid chromatography was performed in a 1μm Ultrapac-TSK Si-150 column (Pharmacia LK Biotech; Baie D'Urfé, PQ), equilibrated with 9.5% isopropanol in hexane, and eluted at 1.2 ml/min.

Untransfected cells and cells transfected with the empty vector or the 1α-OHase cDNA in the anti-sense orientation were negative for $1α,25S(OH)_2D_3$ synthesis. However, cells transfected with the sense 1α-OHase cDNA expression vector produced a vitamin D metabolite that co-eluted on HPLC with the $1α,25(OH)_2D_3$ standard as shown in FIG. 5 at fraction numbers 17–19. Other vitamin D metabolite standards eluted at fractions 6 [$25(OH)D_3$], 8 [$24R,25(OH)_2D_3$], and 13 [$25,26(OH)_3D_3$]. There were no detectable levels of any of these vitamin D metabolites produced by cells transfected with the 1α-OHase cDNA or by any of the controls, as illustrated in FIG. 5.

Figure 6:
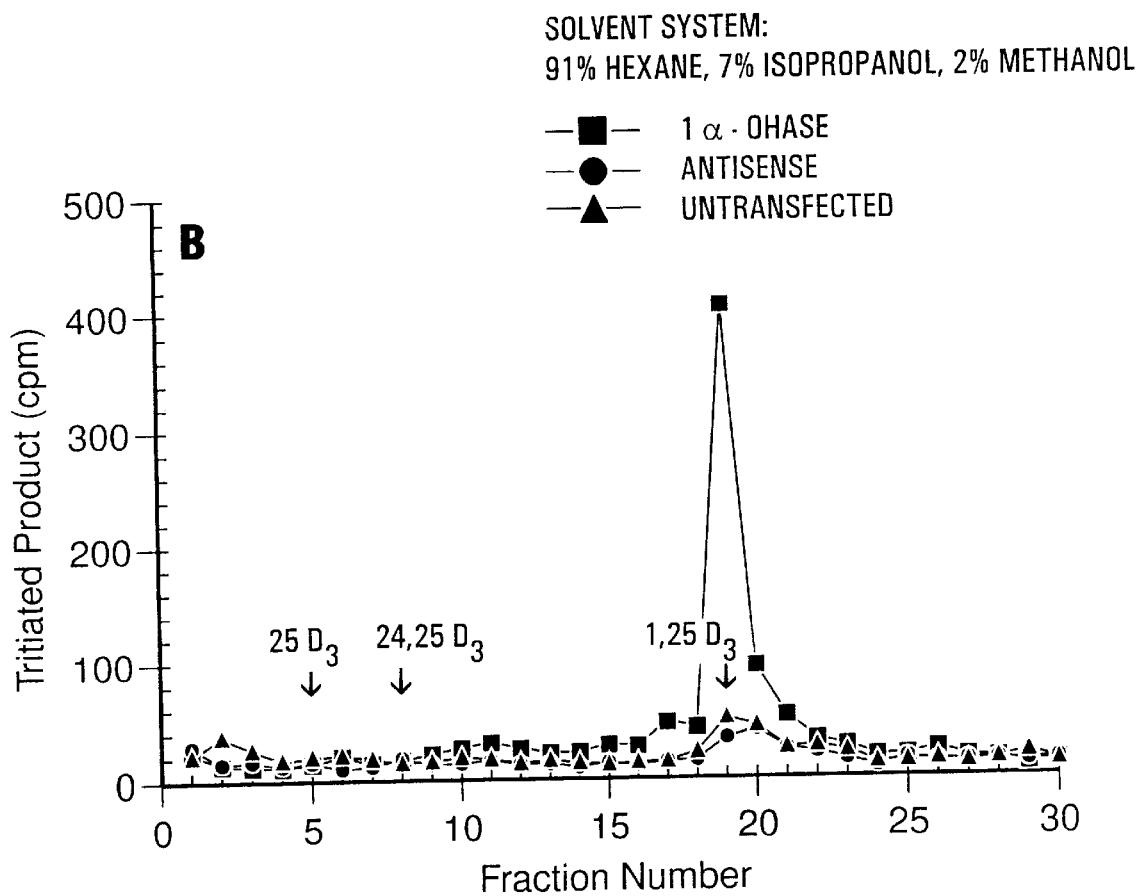
FIG. 6 shows an HPLC elution profile of radiolabelled material co-eluting with reference crystalline $1\alpha,25(OH)_2D_3$ from FIG. 5 rechromatrographed using 91% hexane:7% isopropanol: 2% methanol.

The fractions containing the radiolabeled material co-eluting with reference crystalline $1α,25(OH)_2D_3$ (fractions 17–19) were pooled, evaporated to dryness under a stream of nitrogen and rechromatographed on a slightly less polar solvent system (91% hexane: 7% isopropanol: 2% methanol). Again the putative product co-eluted with the authentic $1α,25(OH)_2D_3$ standard and not with any other vitamin D metabolite standard as shown in FIG. 6. Addition of the cytochrome P450 inhibitor ketoconazole drastically reduced the production of $1α,25(OH)_2D_3$ from cells transfected with the 1-α-OHase cDNA while treatment with N,N'diphenyl-plphenylenediamine, an inhibitor of non-specific oxidation reactions, had no effect. The production of authentic $1α,25(OH)_2D_3$ from cells transfected with the sense cDNA was also assessed using two different radioreceptor assays according to the methods described by Eisman et al, Arch. Biochem. Biophys 176:235–243(1976) and Hollis, Clin. Chem 32:2060–2065 (1986) as well as by mass spectrometry. All methods confirmed that the 1α-OHase clone could produce a vitamin D metabolite indistinguishable from $1α,25(OH)_2D_3$.

EXAMPLE 3

Hormonal Regulation of 1α-OHase Expression

Hormonal regulation of the expression of the 1α-OHase gene in kidney tissue was assessed as follows. In a first series of experiments, vitamin D-replete mice were treated with 0.25 mg/kg/day $1α,25(OH)_2D_3$ or with 25mg/kg/day PTH by way of subcutaneously implanted hormone releasing vehicles (Alzet osmotic minipumps, Alza Corp., Palo Alto Calif.). The kidneys from each group of mice were harvested three days post-implantation. Poly-A+ MRNA was extracted from the tissue as described above. Two hundred nanograms of mRNA was then converted to cDNA in a 20 μl reaction using Superscript II reverse transcriptase (Gibco BRL, Canadian Life Technologies) as recommended by the manufacturer. Five μl of each reverse transcription reaction was then added to a standard 50 μl PCR mixture. The parameters for thermal cycling were as follows: 95° C. for 30 seconds, 65° C. for 1 minute and 72° C. for 1 minute. The upstream primer corresponded to positions 972 to 991 of the rat cDNA while the downstream primer corresponded to nucleotides 1462 to 1480. As a control, parallel PCR reactions were run for each sample group using β-actin primers (Clontech; Palo Alto, Calif.) as per the manufacturer's protocol. PCR products were separated on a 1% agarose gel in TBE. For Northern blot assays, pig kidney cortical-tissue was obtained from vitamin D-deficient animals with induced 1α-OHase activity using the protocol described by Omdahl et al, Arch Diochem Biophys 293: 213–218 (1992) or 1α,25(OH)$_2$D$_3$-treated animals with suppressed 1α-OHase activity using the protocol described by Gray et al, Steroids 55:395–398 (1990). RNA was isolated from frozen tissue by the guanidinium isothiocyanate method described by Chomczynski et al, Anal Biochem. 162:156–159 (1987). Total RNA was size separated on a formaldehyde agarose gels and blotted to a nylon membrane (Biodyne, Pall) prior to hybridization against the rat 1α-OHase clone.

Figure 7:
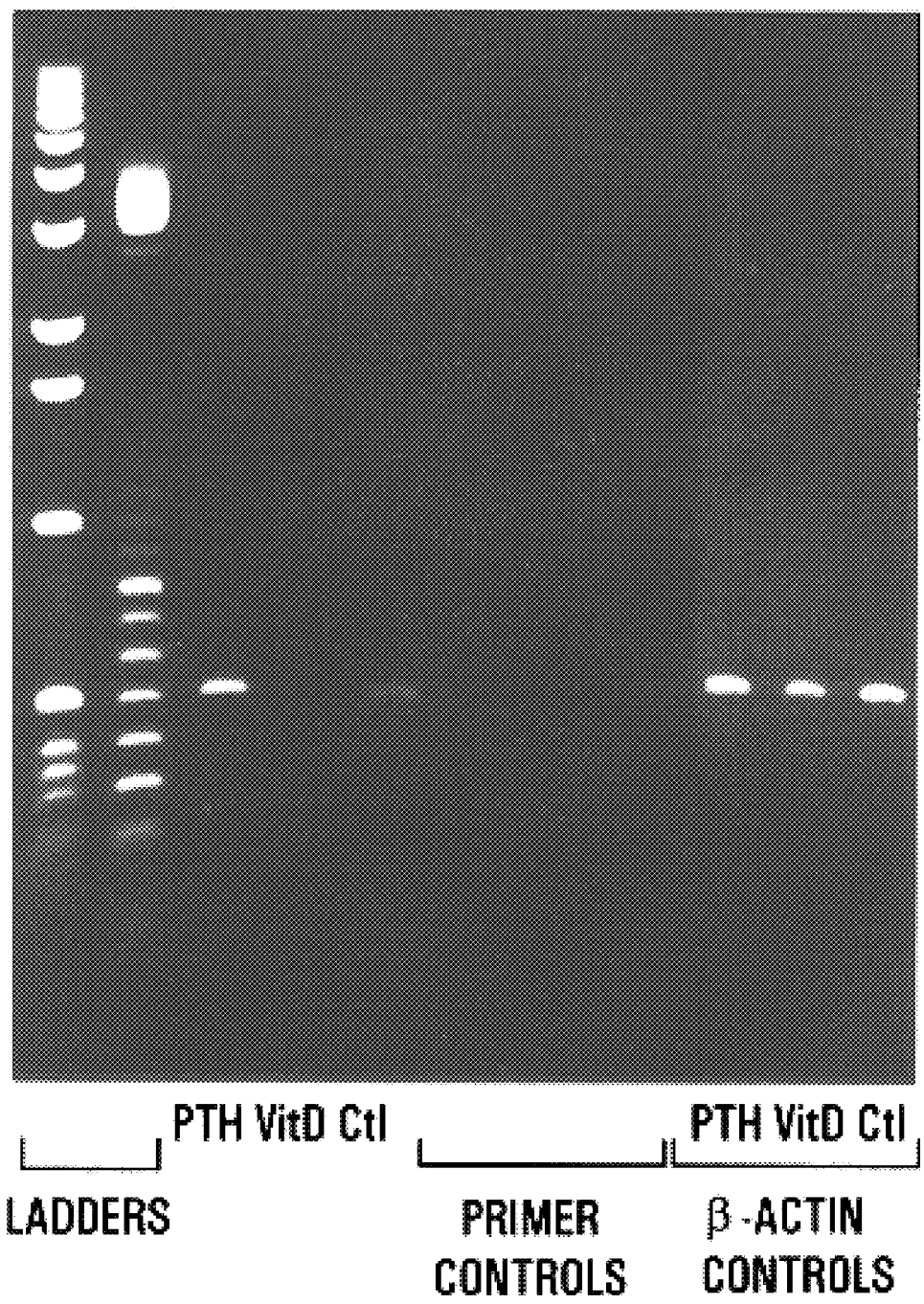
FIG. 7 shows an ethidium bromide-stained agarose gel illustrating the hormonal control of 1α-OHase expression.

The 1α-OHase expression levels were extremely low and the transcript could only be detected using reverse transcription-polymerase chain reaction (RT-PCR) the results of which are shown in FIG. 7. The analysis confirmed an increased expression of the 1α-OHase transcript following PTH treatment, while the expression of the gene in vitamin D treated animals was reduced compared to controls, see FIG. 7. PCR primer controls showed no extraneous PCR products. The RT-PCR assay was performed under semi-quantitative conditions, as β-actin controls permitted equial addition of MRNA to the respective reactions and equal loading of the samples on the agarose gel. Densitometric scanning of the signals revealed a 2.0 fold increase by PTH treatment and a 70% inhibition caused by 1α,25(OH)$_2$D$_3$ administration.

Figure 8:
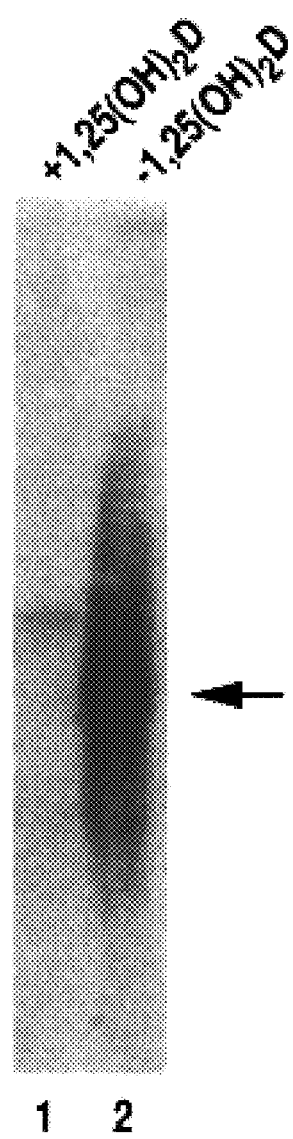
FIG. 8 shows a Northern blot of RNA from kidneys of $1\alpha,25(OH)_2D_3$ treated pigs and vitamin D-deficient pigs.

The expression of the 1α-OHase gene was also analyzed in vitamin D-deprived animals. Young pigs were maintained on a vitamin D-deficient diet and total RNA prepared from kidney tissue. Vitamin D-deficiency drastically increased the expression of the 1α-OHase transcript, as it could easily be detected using Northern blot assay with total RNA, see FIG. 8, lane 2. The 1α-OHase signal was undetectable in vitamin D-treated pigs, see FIG. 8 lane 1.

EXAMPLE 4
1α-OHase from Mouse

The murine 1α-OHase cDNA was cloned and the nearly full-length sequence is shown in FIG. 3. From this murine cDNA clone, the mouse 1α-OHase gene can be easily cloned.

The promoter region is sequenced using techniques known to those skilled in the art. Reporter constructs in which various regions of the 1α-OHase gene promoter have been subcloned upstream of the luciferase reporter gene are engineered. Low levels of expression are circumvented by using a sensitive reporter gene (luciferase) and a vector backbone that includes enhancer sequences (such as Promega's pGL3-enhancer plasmid backbone which has been engineered for studying weak promoters). These constructs are transfected in COS or CV-1 cells. These kidney cells are easily transfected using calcium-phosphate mediated gene Lransfer or lipsosome-based methods. Transfected cells are treated with agonists and the activity of the reporter gene measured. These experiments identify which regions of the 1α-OHase promoter contain the cis-acting elements that confer response to the hormones and cytokines.

The promoter regions identified in this fashion are used as probes in gel retardation assays and DNase footprinting assays to precisely delineate the sequence of the regulatory elements. These assays are performed using nuclear extracts from untreated and hormone-treated kidney cells. The transcription factors that bind the response elements in hormone treated cells are identified by further experiments. The signal transduction cascades implicated in the response to these hormones are known, therefore it is possible to use antibodies directed against known transcription factors to test for their involvement in the regulation of 1α-OHase transcription.

It is also be possible to identify the negative (inhibitory) vitamin D response element (nVDRE) since 1α-OHase expression is strongly repressed by 1α,25(OH)$_2$D$_3$.

EXAMPLE 5
Mapping of the Human 1α-OHase Gene

A human genomic clone for the 1α-OHase enzyme was isolated from a cosmid arrayed chromosome-12 library (L. Deaven, Los Alamos National Laboratory) using the above describe rat cDNA clone as a probe. A positive 35-40 cosmid clone was digested with EcoRl. A 12 kb fragment that hybridized to the rat cDNA clone was identified by Southern Blot analysis. The EcoRl fragment was digested with Sau3A1, cloned into the BamHl site of the pBluescript KS+ phagemid (Stratagene) and exon-positive inserts were identified by colony hybridization using coding-sequence fragments from the rat 1α-OHase clone. DNA fragments were sequence analyzed on an ABI 373A Sequencer. Partial alignment of the human 1α-OHase gene with the rat cDNA was compared over 150 bp and found to be 85% similar, as shown in FIG. 9. Comparable sequence similarity was calculated for additional regions of the genomic fragment, confirming that the clone is a human 1α-OHase homolog.

The human 1α-OHase was mapped to its chromosomal location using fluorescence in situ hybridization (FISH). Lymphocytes isolated from human blood were cultured in AMEM supplemented with 10% fetal calf serum and phytohemagglutinin (PHA) at 37° C. for 68–72 hours. The lymphocyte cultures were treated with bromodeoxyuridine (BrdU) (0.18 mg/ml) to synchronize the cell population. The synchronized cells were washed three times with serum-free medium to release the block and recultured at 37° C. for six hours in AMEM with thymidine (2.5 mg'ml). Cells were harvested and slides made using standard procedures including hypotonic treatment, fix and air-dry. The positive 35–40 kb cosmid clone was biotinylated with DATP using the BioNick Labeling kit (Gibco BRL, Canadian Life Technologies) at 15° C. for one hour.

Figure 10:
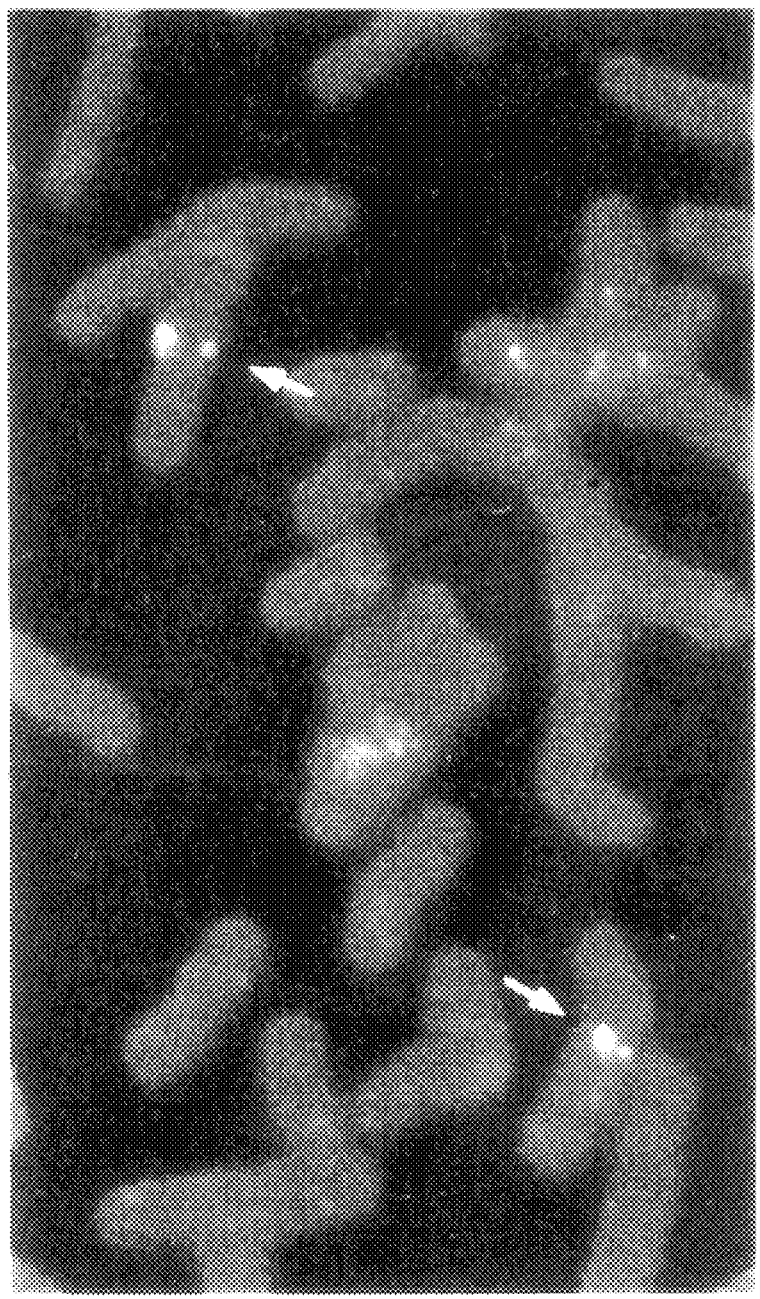
FIG. 10 shows FISH signals of human 1α-OHase probe on human chromosomes.
Figure 11:
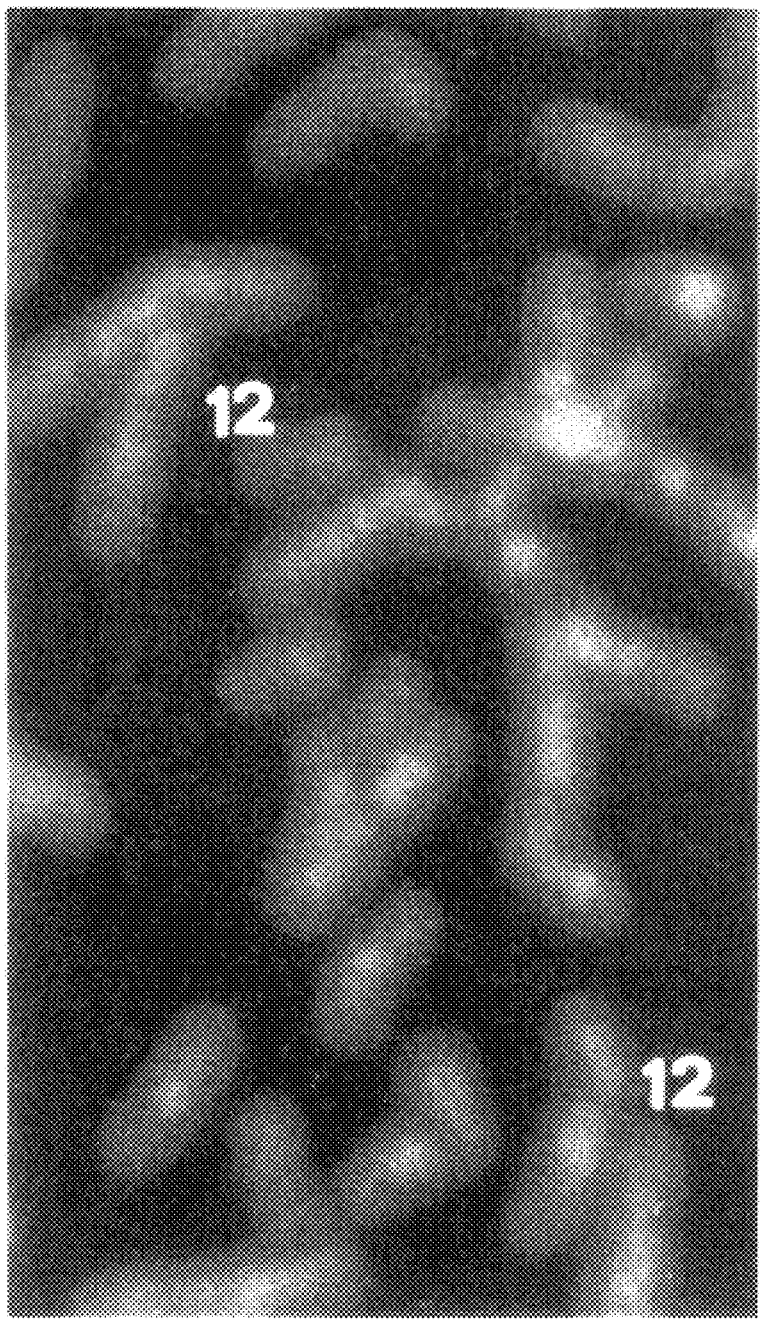
FIG. 11 shows a mitotic figure from FIG. 10 stained with DAP1 to identify chromosome 12.
Figure 12:
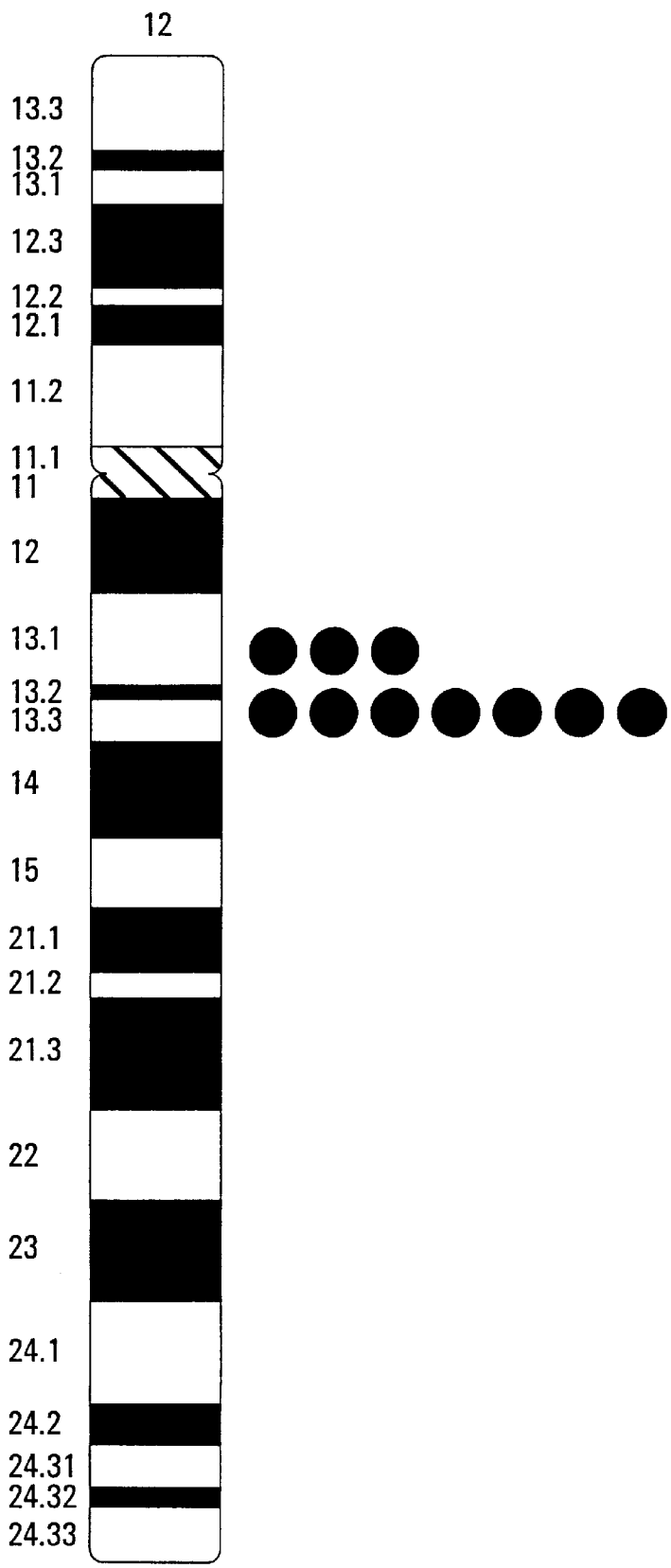
FIG. 12 shows a diagram of FISH mapping results for the human 1α-OHase probe.

The procedure for FISH analysis was performed according to Heng et al, Proc. Natl. Acad. Sci. 89: 9509–9513 (1992), and Heng and Tsui, Chromosoma 102: 325–332 (1993). Briefly, slides were baked at 55° C. for one hour. After RNase treatment, the slides were denatured in 70% formamide, 10% dextran sulphate and human cot I DNA. Probes were loaded on the denatured chromosomal slides after a 15 minute incubation at 37° C. to suppress repetitive sequences. Following overnight hybridization, slides were washed and detected as well us amplified. FISH signals and the DAPI banding pattern were recorded separately by taking photographs, and assignment of the FISH mapping data with chromosomal bands was achieved by superimposing FISH signals with DAPI banded chromosomes. The hybridization efficiency was very high and 96% of checked mitotic figures showed signals on one pair of the chromosomes, as shown in FIG. 10. DAPI banding was used to assign the signals to the long arm of chromosome 12, Rhown in FIG. 11. No other locus was identified by FISH detection under the conditions used, and detailed mapping based on the summary from ten photos located the 1α-OHase gene at human chromosome 12, region q13.1–q13.3, shown in FIG. 12.

EXAMPLE 6
Identification of Mutations in Patients with PDDR

The mapping of the 1α-OHase gene to the PDDR disease locus provides strong evidence that mutations in the 1α-OHase gene are responsible for the PNDR phenotype. Patients with PDDR can be screened for mutations in the 1α-OHase gene using the clones of the invention.

Screening for mutations is facilitated by knowledge of the exon/intron structure of the candidate gene. Exon/intron boundaries have been partially mapped by comparing the sequence of the rat cDNA to that of the cloned human genomic fragment. The 1α-OHase gene is 11 kb and is estimated to have 8 to 10 exons based on the structure of related genes. Five exons and their flanking intervening sequences have been sequenced and are shown in FIG. 4.

Disease-causing mutations in the exons characterized are identified using conformation-sensitive gel electrophoresis (CSGE), according to the method described by Ganguly et al. Pros. Natl. Acad. Sci. 90:10325 (1993), with genomic DNA from blood cells. CSGE uses mildly denaturing solvents such as ethylene glycol and formamide to amplify the tendency of single-base mismatches to produce conformational changes, such as bends, bulges or bubbles in the double helix, and thereby increases the differential migration of DNA heteroduplexes compared to wild type homoduplexes during gel electrophoresis. Control and test DNAs are amplified using sets of primers generating exon.ic segments with around 50 bp of flanking intronic sequences on each side. The total length of the amplified fragments is about 500 bp. The migration of control homoduplexes is compared with the migration of heteroduplexes formed by co-denaturation and re-annealing of test and control amplified samples (heteroduplexes contain one strand of wild-type and oiie strand of mutated DNA). Electrophoresis is performed using 6% polyacrylamide gels polymerized in 10% ethylene glycol/15% formamide. Fragments which are believed to contain point mutations are sequenced by the chain termination method described by Sanger et al, Proc Natl. Acad. Sci 74:5463 (1977), to identify and localize the precise nucleotide change.

In circumstances where CSGE does not detect disease causing mutations due to technical limitations, single-strand conformation polymorphism (SSCP) can be used according to the method described by Spinardi et al, Nucl. Acids Res. 19: 4009 (1991). SSCP relies on conformational changes (conformational polymorphisms that result from altered intrastrand base-pairing). Overlapping DNA fragments of about 200 bp are generated using PCR with appropriate sets of primers and rendered single-stranded by Heating in a denaturing buffer containing formamide. The separated strands are then resolved on non-denaturing polyacrylamide gels. Since single-stranded molecules adopt conformations that are dependent upon their sequence, mutant strands exhibit aberrant mobility compared to control, wild-type strands. Bands with altered mobility are excised from the gel and reamplified for sequencing.

CSGE and SSCP are capable of detecting missense mutations as well as small deletions, insertions, inversions and duplications. Large rearrangements and translocations can be detected using conventional Southern blotting experiments comparing restriction fragments from normal individuals with those from patients with PDDR.

Heterogeneity of mutations in the 1α-OHase gene causing PDDR are characterized by analyzing samples from patients of differing countries of origin.

The precise definition of the functional consequences of the identified mutations requires expression of the mutated sequences in suitable cells followed by biochemical analysis of the mutated proteins.

EXAMPLE 7
Targeted Inactivation of the Mouse 1α-OHase Gene

Homologous recombination in embryonic stem (ES) cells is used to engineer a targeted mutation at the 1α-OHase locus and generate a strain of mice deficient in 1α-OHase enzymatic activity. The resulting animals provide a convenient model for study of PDDR. As well, the mutant animals are used to examine the role played by the enzyme during development.

Homozygous mutant animals are produced by breeding heterozygous mutant animals. Such crosses result in a complete absence of 1α-OHase activity during embryonic development and could lead to the identification of previously unrecognized roles for the 1α-OHase gene and the metabolites affected by its expression. Moreover, the development of homozygous mutants may reveal the influence of other loci which play a role in the PDDR phenotype.

Gene targeting technology, as described by Hogan et al, *Manipulating the Mouse Embryo*, 2nd Ed. (Cold Spring Harbor: Cold Spring Harbor Press, 1994), sometimes referred to as "gene knock-out" relies on the use of pluripotent embryo-derived stem (ES) cells. An inactivating mutation is engineered into a cloned genomic fragment of the target gene and this mutated gene is introduced into ES cells cultured in vitro. The transfected mutant gene will most frequently integrate randomly into the host cell's genome. It is possible, using the technique described by Hogan et al, .supra, to identify and isolate the rare cells that have incorporated the mutant gene at the targeted chromosomal location resulting in a null allele of the target gene. These cells are then micro-injected into the blastocoel cavity of a pre-implantation mouse embryo and the blastocyst is re-implanted into the uterus of a foster mother. Hack-cross breeding enables determination of whether the ES cells have contributed to the germ line of the chimeric animals. The progeny that show ES cell germ line mutation can be interbred to obtain animals that are homozygous for the desired mutation.

The mouse 1α-OHase clone is used in gene knock-out as follows. A mouse 1α-OHase gene is selected which originates from a genomic DNA library of the same mouse strain as used to obtain the ES cell line. Use of DNA from the same strain as the ES cells is known to increase the frequency of homologous recombination. For example, a murine 1α-OHase gene from a liver genomic DNA library of the 129/terSV agouti coat coloured mouse strain can be used since an ES cell line, R1, has been established from that strain. A 1α-OHase targeting vector is designed following the positive-negative double selection scheme described by Mansour et al, Nature 336: 348 (1988). A PGK-neo selection cassette is inserted to replace the exon encoding the heme binding region, thus creating a null allele. This strategy has been successfully utilized to generate null alleles of the 24-OHase gene, which is a similar cytochrome P450 mixed function monooxygenase. The neo expression cassette is placed in the same transcriptional orientation as the 1α-OHase gene, so that the polyadenylation sequence of the neo gene could also serve to polyadenylate, and thereby truncate, any fusion transcript following targeted integration. The PGK-tk cassette is cloned downstream of the region of homology of the construct to select against non-targeted random integration events.

The linearized targeting vector is electroporated into ES cells. Double selection is performed with the aminoglycoside antibiotic G418 and the nucleoside analog gancyclovir. Resistant colonies are picked and used to produce cell lines. The cell lines are screened for the presence of a disrupted 1α-OHase gene by Southern blot analysis after preparation of DNA by the micro-isolation technique of Laird et al. Nucl. Acids Res. 19: 4293 (1991). The ES cell clones carrying the targeted 1α-OHase allele are miiltiplied and then injected into C57BL/6 embryos at the blastocyst stage using standard techniques as described by Hogan et al, supra.

Chimeric animals are identified on the basis of chimeric coat color (agouti patches on a black background). Chimeric males are bred to C57EL/6 females and germ line transmission assessed by the presence of the agouti coat color in the resulting F1 progeny. Animals showing germ line transmission are genotyped by Southern blot analysis of tail DNA according to the method described by Laird et al, supra. Heterozygotes for the mutated allele are mated inter se to produce all three possible genotypes (+/+, +/− and −/−). The morphology of the bones and growth plate from the resulting homozygous animals is studied and compared to the morphology of bones from patients with PDDR. The influence of dietary intake of calcium and phosphate on mineral homeostasis in mutant animals is measured.

The mutation is established on an inbred background rapidly by breeding back founder chimeras showing 100% germline transmission to 129 Sv females as described by Hogan et al., supra. This procedure is faster than backcrossing the mutant progeny onto the 129 Sv background, which requires 16 generations. Inbred strains are compared to outbred is strains. Ditferences in phenotype ot mutant homozygotes suggest the influence of modifier loci that affect the expression of the mutation. Responses to treatment with $1\alpha,25(OH)_2D_3$ between the two genetic backgrounds are then tested. These studies provide an animal model for PDDR which is useful to test modifications or refinements to the therapeutic regimens currently in use.

Mutant homozygotes are treated with $1\alpha,25(OH)_2D_3$ to correct rickets and to allow the homozygotes to survive to adulthood. The role of the 1α-OHase enzyme during embryogenesis is examined by breeding adult mutant homozygotes. When mutant homozygous females are mated to heterozygous males, the resulting litters will be comprised of an equal proportion of homozygous mutants and heterozygous control littermates. Replacement therapy with $1\alpha,25(OH)_2D_3$ should be withdrawn before mating so that gestation will proceed in the complete absence of $1\alpha,25(OH)_2D_3$. Dietary manipulation of mineral intake may be necessary to allow pregnancies to come to term. Pups derived from these matings are genotyped to determine the ratio of transmission of the homozygote −/− genotype. A ratio significantly lower than the Mendelian expectation of 50% reveals embryonic lethality. This possibility can be confirmed by the analysis of the pregnant females at various stages of pregnancy for the presence of dead embryos. Homozygosity of the null mutation can be confirmed by genotyping embryos by PCR.

We claim:

1. An isolated and purified polynucleotide encoding all or a fragment of a P450 moiety of a mammalian 1α-hydrolylase enzyme.

2. An isolated and purified polynucleotide according to claim 1 encoding all or a fragment of the P450 moiety of the 1α-hydroxylase enzyme in rats.

3. An isolated and purified polynucleotide according to claim 1 encoding all or a fragment of the P450 moiety of the 1α-hydroxylase enzyme in mice.

4. An isolated and purified polynucleotide according to claim 1 encoding all or a fragment of the P450 moiety of the 1α-hydroxylase enzyme in humans.

5. The isolated and purified polynucleotide of claim 1 comprising a nucleic acid sequence selected from the sequences shown in FIG. 1 (SEQ ID NO: 1), FIG. 3 (SEQ ID NO: 3) and FIG. 9.

6. An isolated and purified polynucleotide which hybridizes under medium stringency conditions with the polynucleotide of claim 5.

7. An isolated and purified polynucleotide comprising a sequence of an exon of a human gene, said polynucleotide comprising a nucleic acid sequence selected from the sequences shown in FIG. 4 (SEQ ID NOs: 4–8).

8. An isolated and purified polynucleotide selected from:
   a) polynucleotides encoding a P450 moiety of a mammalian 1a-hydroxylase enzyme having a nucleic acid sequence selected from the sequences of FIG. 1 (SEQ ID NO: 1), FIG. 3 (SEQ ID NO: 3) and FIG. 9, and
   b) polynucleotides that hybridize under medium stringency conditions with the polynucleotides of a).

9. An expression vector comprising a polynucleotide of claim 5.

10. An expression vector comprising a polynucleotide of claim 6.

11. An animal cell which has been transformed to express a polynucleotide of claim 5.

12. An animal cell which has been transformed to express a polynucleotide of claim 6.

13. A mammalian cell which has been genetically modified such that its endogenous gene for a 1α-hydroxylase enzyme is incapable of expression.

14. A method of producing 1α-hydroxylase enzyme comprising a step of expressing a polynucleotide of claim 5.

15. A method of producing 1α-hydroxylase enzyme comprising a step of expressing a polynucleotide of claim 6.

16. A method for producing vitamin D metabolites using the polynucleotide of claim 1.

17. A method of diagnosing Vitamin D-related disorders in a patient, said method comprising detecting or quantifying the polynucleotide of claim 1 in a biological sample from said patient.

18. A method of treating Vitamin D-related disorders in a patient, said method comprising administering to said patient an effective amount of the polynucleotide of claim 1.

* * * * *

UNITED STATES PATENT AND TRADEMARK OFFICE
CERTIFICATE OF CORRECTION

PATENT NO. : 6,096,876
DATED : August 1, 2000
INVENTOR(S) : René St-Arnaud and Francis H. Glorieux It is certified that error appears in the above-identified patent and that said Letters Patent is hereby corrected as shown below:

Claim 1,
Line 3, change "hydrolylase" to -- hydroxylase --.

Signed and Sealed this

Thirtieth Day of October, 2001

*Attest:*

NICHOLAS P. GODICI
*Attesting Officer*   Acting Director of the United States Patent and Trademark Office